(12) United States Patent
Zagar et al.

(10) Patent No.: US 7,375,058 B2
(45) Date of Patent: May 20, 2008

(54) HERBICIDAL MIXTURES BASED ON 3-PHENYLURACILS

(75) Inventors: Cyrill Zagar, Mannheim (DE); Bernd Sievernich, Haßloch (DE); Laura Ouakenbush, Holland, PA (US); Richard R. Evans, Greenville, MS (US); Max Landes, Visalia, CA (US); Larry J. Newsom, Greenville, MS (US); Charles L. Ortlip, Durham, NC (US); Matthias Witschel, Bad Dürkheim (DE); Andreas Landes, Römerberg-Heiligenstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 143 days.

(21) Appl. No.: 10/488,977

(22) PCT Filed: Sep. 10, 2002

(86) PCT No.: PCT/EP02/10136

§ 371 (c)(1),
(2), (4) Date: Mar. 9, 2004

(87) PCT Pub. No.: WO03/024221

PCT Pub. Date: Mar. 27, 2003

(65) Prior Publication Data

US 2004/0235665 A1 Nov. 25, 2004

(51) Int. Cl.
*A01N 25/00* (2006.01)
(52) U.S. Cl. .................................... 504/116.1
(58) Field of Classification Search ............... 504/103, 504/104–112, 128, 132, 134, 136, 116.1
See application file for complete search history.

(56) References Cited

U.S. PATENT DOCUMENTS

| 5,084,084 | A | 1/1992 | Satow et al. | |
| 5,154,755 | A | 10/1992 | Satow et al. | |
| 5,571,772 | A | 11/1996 | Willms et al. | |
| 5,700,805 | A | 12/1997 | Schafer et al. | |
| 6,107,252 | A | 8/2000 | Andree et al. | |
| 6,444,613 | B1 * | 9/2002 | Feurer et al. | 504/129 |
| 6,534,492 | B2 * | 3/2003 | Carlsen et al. | 514/183 |
| 6,624,120 | B1 | 9/2003 | Andree et al. | |
| 6,734,139 | B1 * | 5/2004 | Feucht et al. | 504/128 |
| 6,815,398 | B1 | 11/2004 | Andree et al. | |

FOREIGN PATENT DOCUMENTS

| WO | WO 00/78734 | 12/2000 |
| WO | WO 01/34575 | 5/2001 |
| WO | 01/83459 | 11/2001 |

OTHER PUBLICATIONS

Derwent Abst. 96-210261/22 (DE 44 37 197).
Derwent Abst. 96-39400 (DE 195 06 202).

* cited by examiner

*Primary Examiner*—Shelley A. Dodson
(74) *Attorney, Agent, or Firm*—Novak Druce + Quigg LLP

(57) ABSTRACT

Herbicidally active compositions, comprising: A) at least one phenyluracil compound of the formula (I); in which the variables $R^1$-$R^7$ are as defined in the claims, and/or at least one of its agriculturally acceptable salts; and at least one further active compound, selected from B) herbicides of classes b1) to b15): b1) lipid biosynthesis inhibitors; b2) acetolactate synthase inhibitors (ALS inhibitors); b3) photosynthesis inhibitors; b4) protoporphyrinogen-IX oxidase inhibitors; b5) bleacher herbicides; b6) enolpyruvyl shikimate 3-phosphate synthase inhibitors (EPSP inhibitors); b7) glutamine synthetase inhibitors; b8) 7,8-dihydropteroate synthase inhibitors (DHP inhibitors); b9) mitose inhibitors; b10) inhibitors of the synthesis of very long chain fatty acids (VLCFA inhibitors); b11) cellulose biosynthesis inhibitors; b12) decoupler herbicides; b13) auxin herbicides; b14) auxin transport inhibitors; b15) other herbicides selected from the group consisting of benzoylprop, flamprop, flamprop-M, bromobutide, chlorflurenol, cinmethylin, methyldymron, etobenzanid, fosamine, metam, pyributicarb, oxaziclomefone, dazomet, triaziflam and methyl bromide; and safeners selected from: benoxacor, cloquintocet, cyometrinil, dichlormid, dicyclonon, dietholate, fenchlorazole, fenclorim, flurazole, fluxofenim, furilazole, isoxadifen, mefenpyr, mephenate, naplithalic anhydride, 2,2,5-trimethyl-3-(dichloroacetyl)-1,3-oxazolidine, 4-(dichloroacetyl)-1-oxa-4-azaspiro[4.5]decane and oxabetrinil, the agriculturally acceptable salts of the active compounds B and C and the agriculturally acceptable derivatives of the active compounds B and C, provided they have a carboxyl group

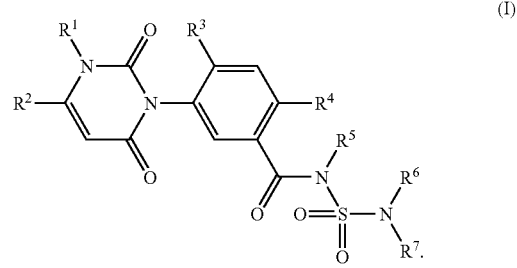

(I)

26 Claims, No Drawings

HERBICIDAL MIXTURES BASED ON 3-PHENYLURACILS

The present invention relates to herbicidally active compositions comprising 3-phenyluracils and at least one further active compound selected from herbicidally active compounds and safeners.

In crop protection products, it is desirable in principle to increase the specificity and the reliability of the action of active compounds. In particular, it is desirable for the crop protection product to control the harmful plants effectively and, at the same time, to be tolerated by the useful plants in question.

Various publications have described 3-phenyluracils as being highly effective herbicides. However, their compatibility with dicotyledonous crop plants such as cotton, oilseed rape and some graminaceous plants such as barley, millet, corn, rice, wheat and sugar cane is not always satisfactory, i.e. in addition to the harmful plants, the crop plants are also damaged to an extent which is not acceptable. It is possible to spare the useful plants by lowering the application rates; however the extent of the control of harmful plants is naturally also reduced.

It is known that certain combinations of different herbicides with specific action result in an enhanced activity of a herbicide component by synergism. As a consequence, it is possible to reduce the application rates of herbicidally active compounds required for controlling the harmful plants.

Furthermore, it is known that in some cases better crop plant compatibility can be achieved by joint application of specifically acting herbicides with organic active compounds, some of which are themselves herbicidally active. In these cases, the active compounds act as antidote or antagonist, and, owing to the fact that they can reduce or even prevent damage to the crop plants, they are also referred to as safeners.

DE 195 06 202 describes herbicidal compositions comprising a herbicidally effective amount of a 3-phenyluracil and an antagonistically effective amount of a 3-(2-chlorophenylmethyl)-1-(1-methyl-1-phenylethyl)urea and/or a 1-(1-methyl-1-phenylethyl)-3-(4-tolyl)urea.

3-Phenyluracils of the formula I:

in which the variables $R^1$-$R^7$ are as defined below:

$R^1$ is methyl or $NH_2$;
$R^2$ is $C_1$-$C_2$-haloalkyl;
$R^3$ is hydrogen or halogen;
$R^4$ is halogen or cyano;
$R^5$ is hydrogen, cyano, $C_1$-$C_6$-alkyl, $C_1$-$C_6$-alkoxy, $C_1$-$C_4$-alkoxy-$C_1$-$C_4$-alkyl, $C_3$-$C_7$-cycloalkyl, $C_3$-$C_6$-alkenyl, $C_3$-$C_6$-alkynyl or benzyl which is unsubstituted or substituted by halogen or alkyl;

$R^6$, $R^7$ independently of one another are hydrogen, $C_1$-$C_6$-alkyl, $C_1$-$C_6$-alkoxy, $C_3$-$C_6$-alkenyl, $C_3$-$C_6$-alkynyl, $C_3$-$C_7$-cycloalkyl, $C_3$-$C_7$-cycloalkenyl, phenyl or benzyl, where each of the 8 abovementioned substituents is unsubstituted or may be substituted by 1 to 6 halogen atoms and/or by one, two or three groups selected from: OH, $NH_2$, CN, $CONH_2$, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfonyl, $C_1$-$C_4$-haloalkylsulfonyl, $C_1$-$C_4$-alkylamino, di($C_1$-$C_4$-alkyl)amino, formyl, $C_1$-$C_4$-alkylcarbonyl, $C_1$-$C_4$-alkoxycarbonyl, $C_1$-$C_4$-alkylaminocarbonyl, di($C_1$-$C_4$-alkyl)aminocarbonyl, $C_3$-$C_7$-cycloalkyl, phenyl and benzyl; or $R^6$, $R^7$ together with the nitrogen atom form a 3-, 4-, 5-, 6- or 7-membered saturated or unsaturated nitrogen heterocycle which may be substituted by 1 to 6 methyl groups and which may contain 1 or 2 further heteroatoms selected from the group consisting of nitrogen, oxygen and sulfur as ring members, and their agriculturally acceptable salts are disclosed in the earlier patent application PCT/EP 01/04850.

It is an object of the present invention to increase the herbicidal activity of 3-phenyluracils of the formula I against undesirable harmful plants and to improve simultaneously their compatibility with useful plants.

We have found that this object is achieved, surprisingly, by compositions comprising at least one 3-phenyluracil of the formula I and/or at least one agriculturally acceptable salt of I and at least one further active compound, selected from B) herbicides of classes b1) to b15):
  b1) lipid biosynthesis inhibitors;
  b2) acetolactate synthase inhibitors (ALS inhibitors);
  b3) photosynthesis inhibitors;
  b4) protoporphyrinogen-IX oxidase inhibitors;
  b5) bleacher herbicides;
  b6) enolpyruvyl shikimate 3-phosphate synthase inhibitors (EPSP inhibitors);
  b7) glutamine synthetase inhibitors;
  b8) 7,8-dihydropteroate synthase inhibitors (DHP inhibitors);
  b9) mitose inhibitors;
  b10) inhibitors of the synthesis of long chain fatty acids (VLCFA inhibitors);
  b11) cellulose biosynthesis inhibitors;
  b12) decoupler herbicides;
  b13) auxin herbicides;
  b14) auxin transport inhibitors;
  b15) other herbicides selected from the group consisting of benzoylprop, flamprop, flamprop-M, bromobutide, chlorflurenol, cinmethylin, methyldymuron, etobenzanid, fosamine, metam, pyributicarb, oxaziclomefone, dazomet, triaziflam and methyl bromide;

and

C) safeners selected from: benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, 2,2,5-trimethy-1-3-(dichloroacetyl)-1,3-oxazolidine (R-29148), 4-(dichloroacetyl)-1-oxa-4-azaspiro[4.5]decane (AD-67; MON 4660) and oxabetrinil, the agriculturally acceptable salts of the active compounds B and C and the agriculturally acceptable derivatives of the active compounds B and C, provided they have a carboxyl group.

The invention relates in particular to compositions in the form of herbicidally active crop protection compositions comprising a herbicidally effective amount of at least one mixture of A with B and/or C, as defined above, and at least one liquid and/or solid carrier and, if desired, one or more surfactants and, if desired, one or more further auxiliaries customary for crop protection compositions. The invention also relates to compositions in the form of a crop protection composition formulated as a 2-component composition comprising a first component which comprises the active compound A, a solid or liquid carrier and, if appropriate, one or more surfactants, and a second component which comprises at least one further active compound selected from the herbicides B and the safeners C, a solid or liquid carrier and, if appropriate, one or more surfactants, where both components may additionally comprise further auxiliaries customary for crop protection compositions.

The invention furthermore relates to a method for controlling undesirable vegetation, in particular in crops of cereals, corn, soybeans, rice, oilseed rape, cotton, potatoes, groundnuts or in perennial crops, and also in crops which, by genetic engineering or by breeding, are resistant to one or more herbicides or to attack by insects. The invention also relates to a method for the desiccation or defoliation of plants. In the latter methods it is immaterial whether the herbicidally active compounds of components A) and B) and/or C) are formulated and applied jointly or separately, and, in the case of separate application, in which order the application takes place.

The organic moieties mentioned in the definition of the substituents $R^2$, $R^5$, $R^6$, $R^7$ in formula I and $R^8$ to $R^{13}$ in formula II or as radicals on cycloalkyl, phenyl or heterocyclic rings are—like the term halogen—collective terms for individual enumerations of the individual group members. All hydrocarbon chains, i.e. all alkyl, haloalkyl, cycloalkyl, alkoxy, haloalkoxy, alkylamino, alkylthio, haloalkylthio, alkylsulfinyl, haloalkylsulfinyl, alkylsulfonyl, haloalkylsulfonyl, alkenyl and alkynyl groups and corresponding moieties in larger groups such as alkylcarbonyl, alkylaminocarbonyl, dialkylaminocarbonyl, alkoxycarbonyl, etc., can be straight-chain or branched, the prefix $C_n$-$C_m$ denoting in each case the possible number of carbon atoms in the group. Halogenated substituents preferably carry one, two, three, four or five identical or different halogen atoms. The term halogen denotes in each case fluorine, chlorine, bromine or iodine.

Examples of other meanings are:

$C_1$-$C_4$-alkyl: $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_4$-haloalkyl: a $C_1$-$C_4$-alkyl radical as mentioned above which is partially or fully substituted by fluorine, chlorine, bromine and/or iodine, i.e., for example, $CH_2F$, $CHF_2$, $CF_3$, $CH_2Cl$, dichloromethyl, trichloromethyl, chlorofluormethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_6$-haloalkyl: a $C_1$-$C_6$-alkyl radical as mentioned above which is partially or fully substituted by fluorine, chlorine, bromine and/or iodine, i.e., for example, one of the radicals mentioned under $C_1$-$C_4$-haloalkyl and also 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl;

$C_1$-$C_4$-alkoxy: $OCH_3$, $OC_2H_5$, n-propoxy, $OCH(CH_3)_2$, n-butoxy, $OCH(CH_3)$—$C_2H_5$, $OCH_2$-$CH(CH_3)_2$ or $OC(CH_3)_3$, preferably $OCH_3$, $OC_2H_5$ or $OCH(CH_3)_2$;

$C_1$-$C_4$-haloalkoxy: a $C_1$-$C_4$-alkoxy radical as mentioned above which is partially or fully substituted by fluorine, chlorine, bromine and/or iodine, i.e., for example, $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, $OCF_2$-$C_2F_5$, 1-($CH_2F$)-2-fluoroethoxy, 1-(CH2Cl)-2-chloroethoxy, 1-($CH_2Br$)-2-bromoethoxy, 4-fluorobutoxy, 4-chlorobutoxy, 4-bromobutoxy or nonafluorobutoxy, preferably $OCHF_2$, $OCF_3$, dichlorofluoromethoxy, chlorodifluoromethoxy or 2,2,2-trifluoroethoxy;

$C_1$-$C_4$-alkylthio: $SCH_3$, $SC_2H_5$, n-propylthio, $SCH(CH_3)_2$, n-butylthio, $SCH(CH_3)$—$C_2H_5$, $SCH_2$—$CH(CH_3)$ 2 or $SC(CH_3)_3$, preferably $SCH_3$ or $SC_2H_5$;

$C_1$-$C_4$-haloalkylthio: a $C_1$-$C_4$-alkylthio radical as mentioned above which is partially or fully substituted by fluorine, chlorine, bromine and/or iodine, i.e., for example, $SCH_2F$, $SCHF_2$, $SCH_2Cl$, $SCH(Cl)_2$, $SC(Cl)_3$, $SCF_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, $2,2,^2$-trichloroethylthio, $SC_2F_5$, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$-$C_2F_5$, $SCF_2$-$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or $SCF_2$-$CF_2$-$C_2F_5$, preferably $SCHF_2$, SCF₃, dichlorofluoromethylthio, chlorodifluoromethylthio or 2,2,2-trifluoroethylthio;

$C_1$-$C_4$-alkoxy-$C_1$-$C_4$-alkyl: $C_1$-$C_4$-alkyl which is substituted by $C_1$-$C_4$-alkoxy—as mentioned above—, i.e., for example, CH₂-OCH₃, CH₂-OC₂H₅, n-propoxymethyl, CH₂-OCH(CH₃)₂, n-butoxymethyl, (1-methylpropoxy)methyl, (2-methylpropoxy)methyl, CH₂-OC(CH₃)₃, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably CH₂-OCH₃, CH₂-OC₂H₅, 2-methoxyethyl or 2-ethoxyethyl;

($C_1$-$C_4$-alkyl)carbonyl: CO-CH₃, CO-C₂H₅, CO-CH₂-C₂H₅, CO-CH(CH₃)₂, n-butylcarbonyl, CO-CH(CH₃)-C₂H₅, CO-CH₂-CH(CH₃)₂ or CO-C(CH₃)₃, preferably CO-CH₃ or CO-C₂H₅;

($C_1$-$C_4$-alkoxy)carbonyl: CO-OCH3, CO-OC₂H₅, n-propoxycarbonyl, CO-OCH(CH₃)₂, n-butoxycarbonyl, CO-OCH(CH₃)-C₂H₅, CO-OCH₂-CH(CH₃)₂ or CO-OC(CH₃)₃, preferably CO-OCH₃ or CO-OC₂H₅;

$C_1$-$C_4$-alkylsulfinyl: SO-CH₃, SO-C₂H₅, SO-CH₂-C₂H₅, SO-CH(CH₃)₂, n-butylsulfinyl, SO-CH(CH₃)-C₂H₅, SO-CH₂-CH(CH₃)₂ or SO-C(CH₃)₃, preferably SO-CH₃ or SO-C₂H₅;

$C_1$-$C_4$-haloalkylsulfinyl: a $C_1$-$C_4$-alkylsulfinyl radical—as mentioned above—which is partially or fully substituted by fluorine, chlorine, bromine and/or iodine, i.e., for example, SO-CH₂F, SO-CHF₂, SO-CF₃, SO-CH₂Cl, SO-CH(Cl)₂, SO-C(Cl)₃, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl, SO-C₂F₅, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, SO-CH₂-C₂F₅, SO-CF₂-C₂F₅, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl or nonafluorobutylsulfinyl, preferably SO-CF₃, SO-CH₂Cl or 2,2,2-trifluoroethylsulfinyl;

$C_1$-$C_4$-alkylsulfonyl: SO₂-CH₃, SO₂-C₂H₅, SO₂-CH₂-C₂H₅, SO₂-CH(CH₃)₂, n-butylsulfonyl, SO₂-CH(CH₃)-C₂H₅, SO₂-CH₂-CH(CH₃)₂ or S0₂-C(CH₃)3, preferably SO₂-CH₃ or SO₂-C₂H₅;

$C_1$-$C_4$-haloalkylsulfonyl: a $C_1$-$C_4$-alkylsulfonyl radical—as mentioned above—which is partially or fully substituted by fluorine, chlorine, bromine and/or iodine, i.e., for example, SO₂-CH₂F, SO₂-CHF₂, SO₂-CF₃, SO₂-CH₂Cl, SO₂-CH(Cl)₂, SO-C(Cl)₃, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, SO₂-C₂F₅, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, SO₂-CH₂-C₂F₅, SO₂-CF₂-C₂F₅, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl, preferably SO₂-CF₃, SO₂-CH₂Cl or 2,2,2-trifluoroethylsulfonyl;

$C_1$-$C_4$-alkylamino: NH(CH₃), NH(C₂H₅), propylamino, NH[CH(CH₃)₂], butylamino, 1-methylpropylamino, 2-methylpropylamino, NH[C(CH₃)₃];

di($C_1$-$C_4$-alkyl)amino: N(CH₃)₂, N(C₂H₅)₂, N,N-dipropylamino, N[CH(CH₃)₂]₂, N,N-dibutylamino, N,N-di(1-methylpropyl)amino, N,N-di(2-methylpropyl)amino, N[C(CH₃)₃]₂, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl) amino, N-(1,1-dimethylethyl)-N-(1-methylpropyl)amino or N-(1,1-dimethylethyl)-N-(2-methylpropyl)amino, preferably N(CH₃)₂ or N(C₂H₅);

$C_1$-$C_4$-alkylaminocarbonyl: for example methylaminocarbonyl, ethylaminocarbonyl, 1-methylethylaminocarbonyl, propylaminocarbonyl, butylaminocarbonyl, 1-methylpropylaminocarbonyl, 2-methylpropylaminocarbonyl, 1,1-dimethylethylaminocarbonyl;

di($C_1$-$C_4$-alkyl)aminocarbonyl: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(1-methylpropyl)aminocarbonyl, N,N-di(2-methylpropyl) aminocarbonyl, N,N-di(1,1-dimethylethyl) aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl) aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl) aminocarbonyl, N-butyl-N-(1-methylpropyl)aminocarbonyl, N-butyl-N-(2-methylpropyl)aminocarbonyl, N-butyl-N-(1,1-dimethylethyl) aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

$C_3$-$C_6$-alkenyl: prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_3$-$C_6$-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, preferably prop-2-yn-1-yl;

$C_3$-$C_7$-cycloalkyl: cyclopropyl, cyclobutyl, cyclopentyl, cyclohexyl or cycloheptyl;

$C_3$-$C_7$-cycloalkyl which contains-a carbonyl or thiocarbonyl ring member: for example cyclobutanon-2-yl, cyclobutanon-3-yl, cyclopentanon-2-yl, cyclopentanon-3yl, cyclohexanon-2-yl, cyclohexanon-4-yl, cycloheptanon-2-yl, cyclooctanon-2-yl, cyclobutanethion-2-yl, cyclobutanethion-3-yl, cyclopentanethion-2-yl, cyclopentanethion-3-yl, cyclohexanethion-2-yl, cyclohexanethion-4-yl, cycloheptanethion-2-yl or cyclooctanethion-2-yl, preferably cyclopentanon-2-yl or cyclohexanon-2-yl.

Preferred herbicides B which can be used according to the present invention in combination with the 3-phenyluracils of the formula I are:

b1) from the group of the lipid biosynthesis inhibitors: chlorazifop, clodinafop, clofop, cyhalofop, diclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate and bensulide;

b2) from the group of the ALS inhibitors: amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac;

b3) from the group of the photosynthesis inhibitors: atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluron, phenobenzuron, siduron, tetrafluron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate, and pyridafol;

b4) from the group of the protoporphyrinogen-IX oxidase inhibitors: acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen and etnipromid;

b5) from the group of the bleacher herbicides: metflurazon, norflurazon, flufenican, diflufenican, picolinafen, beflubutamid, fluridone, flurochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-($^3$-trifluoromethylphenoxy)-2-(4-trifluoromethylphenyl)pyrimidine, and also 3-heterocyclyl-substituted benzoyl derivatives of the formula II

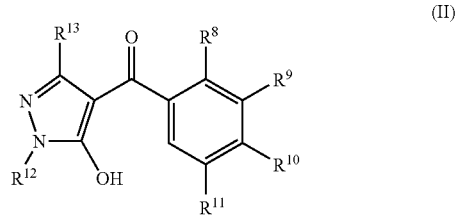

(II)

in which the variables $R^8$ to $R^{13}$ are as defined below:

$R^8$, $R^{10}$ are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl or $C_1$-$C_6$-alkylsulfonyl;

$R^9$ is a heterocyclic radical selected from the group consisting of: thiazol-2-yl, thiazol-4-yl, thiazol-5-yl, isoxazol-3-yl, isoxazol-4-yl, 10 isoxazol-5-yl, 4,5-dihydroisoxazol-3-yl, 4,5-dihydroisoxazol-4-yl and 4,5-dihydroisoxazol-5-yl, where the nine radicals mentioned may be unsubstituted or mono- or polysubstituted, e.g. mono-, di-, tri- or tetrasubstituted, by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;

$R^{11}$ is hydrogen, halogen or $C_1$-$C_6$-alkyl;

$R^{12}$ is $C_1$-$C_6$-alkyl;

$R^{13}$ is hydrogen or $C_1$-$C_6$-alkyl.

b6) from the group of the EPSP synthase inhibitors: glyphosate;

b7) from the group of the glutamine synthase inhibitors: glufosinate and bilanaphos;

b8) from the group of the DHP synthase inhibitors: asulam;

b9) from the group of the mitose inhibitors: benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;

b10) from the group of the VLCFA inhibitors: acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane;

b11) from the group of the cellulose biosynthesis inhibitors: dichlobenil, chlorthiamid, isoxaben and flupoxam;

b12) from the group of the decoupler herbicides: dinofenate, dinoprop, dinosam, dinoseb, dinoterb, DNOC, etinofen and medinoterb;

b13) from the group of the auxin herbicides: clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quinclorac, quinmerac, clopyralid, fluroxypyr, picloram, triclopyr and benazolin;

b14) from the group of the auxin transport inhibitors: naptalam, diflufenzopyr;

b15) benzoylprop, flamprop, flamprop-M, bromobutide, chlorflurenol, cinmethylin, methyldymron, etobenzanid, fosamine, metam, pyributicarb, oxaziclomefone, dazomet, triaziflam and methyl bromide.

The active compounds B of groups b1) to b15) and the active compounds C are known herbicides and safeners, see, for example, The Compendium of Pesticide Common Names (http://www.hclrss.demon.co.uk/index.html); Farm Chemicals Handbook 2000 Vol. 86, Meister Publishing Company, 2000; B. Hock, C. Fedtke, R. R. Schmidt, Herbizide, Georg Thieme Verlag, Stuttgart 1995; W. H. Ahrens, Herbicide Handbook, 7th Edition, Weed Science Society of America, 1994; and K. K. Hatzios, Herbicide Handbook, Supplement to 7th Edition, Weed Science Society of America, 1998. 2,2,5-Trimethyl-3-(dichloroacetyl)-1,3-oxazolidine [CAS No. 52836-31-4] is also known under the name R-29148. 4-(Dichloroacetyl)-1-oxa-4-azaspiro[4.5]decane [CAS No. 71526-07-03] is also known under the names AD-67 and MON 4660. The bleacher herbicides of the formula II described below are disclosed in WO 96/26202, WO 97/41116, WO 97/41117 and WO 97/41118.

The categorization of the active compounds according to their mode of action is based on current understanding. If an active compound acts by more than one mode of action, this substance was assigned to only one mode of action.

If the phenyluracils I, the herbicides B and/or the safeners C are capable of forming geometrical isomers, for example E/Z isomers, it is possible to use both the pure isomers and mixtures thereof in the compositions according to the invention. If the phenyluracils I, the herbicides B and/or the safeners C have one or more centers of chirality and, as a consequence, are present as enantiomers or diastereomers, it is possible to use both the pure enantiomers and diastereomers and their mixtures in the compositions according to the invention.

If the phenyluracils I, the herbicides B and/or the safeners C have functional groups which can be ionized, they can also be used in the form of their agriculturally acceptable salts. In general, the salts of those cations or the acid addition salts of those acids are suitable whose cations and anions, respectively, have no adverse effect on the action of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri ($C_1$-$C_4$-alkyl) sulfoxonium.

It is possible to use, for example, the active compounds of the formulae I and II and chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, propaquizafop, quizalofop, quizalofop-P, trifop, alloxydim, butroxydim, clethodim, cloproxydim, cycloxydim, profoxydim, sethoxydim, tepraloxydim, tralkoxydim, amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, propoxycarbazon, flucarbazon, imazamethabenz, imazamox, imazapic, imazapyr, imazaquin, imazethapyr, cloransulam, diclosulam, florasulam, flumetsulam, metosulam, penoxsulam, bispyribac, pyrithiobac, pyriminobac, bentazon, acifluorfen, ethoxyfen, fluoroglycofen, fomesafen, halosafen, lactofen, pyraflufen, flumiclorac, fluthiacet, carfentrazone, flufenpyr, mesotrione, sulcotrione, glyphosate, glufosinate, bilanaphos, clomeprop, 2,4-D, 2,4-DB, dichlorprop, dichlorprop-P, MCPA, MCPB, mecoprop, mecoprop-P, 2,4,5-T, chloramben, dicamba, 2,3,6-TBA, tricamba, quinclorac, quinmerac, clopyralid, fluroxypyr, picloram, triclopyr, naptalam, diflufenzopyr, cloquintocet, fenchlorazole, isoxadifen and mefenpyr, if desired as salts of the agriculturally useful cations mentioned above, in the compositions according to the invention.

Anions of useful acid addition salts are primarily chloride, bromide, fluoride, iodide, hydrogen sulfate, methyl sulfate, sulfate, dihydrogen phosphate, hydrogen phosphate, nitrate, dicarbonate, carbonate, hexafluorosilicate, hexafluorophosphate, benzoate and the anions of $C_1$-$C_4$-alkanoic acids, preferably formate, acetate, propionate and butyrate.

In the compositions according to the invention, the active compounds cyperquat, diethamquat, difenzoquat, diquat, morfamquat and paraquat are usually employed as salts of the agriculturally useful anions mentioned above.

In the compositions according to the invention, the active compounds which carry a carboxyl group can, instead of the active compounds mentioned above, also be employed in the form of an agriculturally acceptable derivative, for example as amides such as mono- or di-$C_1$-$C_6$-alkylamides or arylamides, as esters, for example as allyl esters, propargyl esters, $C_1$-$C_{10}$-alkyl esters or alkoxyalkyl esters, and also as thioesters, for example as $C_1$-$C_{10}$-alkyl thioesters. Examples of active compounds having a COOH group which can also be employed as derivatives are: chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, propaquizafop, quizalofop, quizalofop-P, trifop, bensulfuron, chlorimuron, ethametsulfuron, flupyrsulfuron, halosulfuron, iodosulfuron, mesosulfuron, metsulfuron, primisulfuron, pyrazosulfuron, sulfometuron, thifensulfuron, tribenuron, triflusulfuron, imazamethabenz, imazamox, imazapic, imazapyr, imazaquin, imazethapyr, cloransulam, bispyribac, pyrithiobac, pyriminobac, acifluorfen, ethoxyfen, fluoroglycofen, lactofen, pyraflufen, flumiclorac, fluthiacet, carfentrazone, flufenpyr, clomeprop, 2,4-D, 2,4-DB, dichlorprop, dichlorprop-P, MCPA, MCPB, mecoprop, mecoprop-P, 2,4,5-T, chloramben, dicamba, 2,3,6-TBA, tricamba, quinclorac, quinmerac, clopyralid, fluroxypyr, picloram, triclopyr, naptalam, diflufenzopyr, cloquintocet, fenchlorazole, isoxadifen and mefenpyr.

Preferred mono- and di-$C_1$-$C_6$-alkylamides are the methyl- and the dimethylamides. Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-c1-$C_4$-alkyl esters are the straight-chain or branched $C_1$-$C_4$-alkoxyethyl esters, for example the methoxyethyl, ethoxyethyl or butoxyethyl esters. An example of the straight-chain or branched $C_1$-$C_{10}$-alkyl thioesters is the ethyl thioester.

Among the 3-phenyluracils of the formula I, preference is given to those in which the variables $R^1$ to $R^7$ independently of one another, but preferably combined, have the meanings given below:
$R^1$ is methyl or $NH_2$;
$R^2$ is trifluoromethyl;
$R^3$ is hydrogen, fluorine or chlorine in particular flourine;
$R^4$ is halogen or cyano in particular chlorine or cyano;
$R^5$ is hydrogen;
$R^6$, $R^7$ independently of one another are hydrogen, $C_1$-$C_6$-alkyl, $C_3$-$C_6$-alkenyl, $C_3$-$C_6$-alkynyl, $C_3$-$C_7$-cycloalkyll $C_3$-$C_7$-cycloalkenyl, phenyl or benzyl or
$R^6$, $R^7$ together with the nitrogen atom form a pyrrolidine, piperidine, morpholine, N-methylpiperazine or perhydroazepine ring.
$R^6$, $R^7$ are in particular identical or different $C_1$-$C_6$-alkyl radicals.

In a particularly preferred embodiment of the invention, the compositions comprise at least one 3-phenyluracil I in which the variables $R^1$ to $R^7$ in formula I have the following meanings (hereinbelow also referred to as phenyluracils Ia):
$R^1$ is methyl;
$R^2$ is trifluoromethyl;
$R^3$ is fluorine;
$R^4$ is chlorine;
$R^5$ is hydrogen;
$R^6$1 $R^7$ independently of one another are $C_1$-$C_6$-alkyl.

In another particularly preferred embodiment of the invention, the compositions comprise at least one 3-phenyluracil I in which the variables $R^1$ to $R^7$ in formula I have the meanings below (hereinbelow also referred to as phenyluracils Ib):
$R^1$ is $NH_2$;
$R^2$ is trifluoromethyl;
$R^3$ is fluorine;
$R^4$ is chlorine;
$R^5$ is hydrogen;
$R^6$, $R^7$ independently of one another are $C_1$-$C_6$-alkyl.

Examples of particularly preferred herbicides Ia or Ib are the compounds of the formula I' listed below in which $R^1$, $R^6$ and $R^7$ together have the meanings given in one row of Table A (compounds I.1 to I.74).

| Phenyluracil I | R¹ | R⁶ | R⁷ |
|---|---|---|---|
| I.1 | methyl | methyl | methyl |
| I.2 | amino | methyl | methyl |
| I.3 | methyl | methyl | ethyl |
| I.4 | amino | methyl | ethyl |
| I.5 | methyl | methyl | propyl |
| I.6 | amino | methyl | propyl |
| I.7 | methyl | methyl | isopropyl |
| I.8 | amino | methyl | isopropyl |
| I.9 | methyl | methyl | butyl |
| I.10 | amino | methyl | butyl |
| I.11 | methyl | methyl | s-butyl |
| I.12 | amino | methyl | s-butyl |
| I.13 | methyl | methyl | isobutyl |
| I.14 | amino | methyl | isobutyl |
| I.15 | methyl | methyl | t-butyl |
| I.16 | amino | methyl | t-butyl |
| I.17 | methyl | methyl | n-pentyl |
| I.18 | amino | methyl | n-pentyl |
| I.19 | methyl | methyl | n-hexyl |
| I.20 | amino | methyl | n-hexyl |
| I.21 | methyl | methyl | allyl |
| I.22 | amino | methyl | allyl |
| I.23 | methyl | methyl | propargyl |
| I.24 | amino | methyl | propargyl |
| I.25 | methyl | methyl | phenyl |
| I.26 | amino | methyl | phenyl |
| I.27 | methyl | methyl | benzyl |
| I.28 | amino | methyl | benzyl |
| I.29 | methyl | ethyl | ethyl |
| I.30 | amino | ethyl | ethyl |
| I.31 | methyl | ethyl | propyl |
| I.32 | amino | ethyl | propyl |
| I.33 | methyl | ethyl | isopropyl |
| I.34 | amino | ethyl | isopropyl |
| I.35 | methyl | ethyl | butyl |
| I.36 | amino | ethyl | butyl |
| I.37 | methyl | ethyl | n-pentyl |
| I.38 | amino | ethyl | n-pentyl |
| I.39 | methyl | ethyl | n-hexyl |
| I.40 | amino | ethyl | n-hexyl |
| I.41 | methyl | propyl | propyl |
| I.42 | amino | propyl | propyl |
| I.43 | methyl | propyl | isopropyl |
| I.44 | amino | propyl | isopropyl |
| I.45 | methyl | propyl | butyl |
| I.46 | amino | propyl | butyl |
| I.47 | methyl | propyl | n-pentyl |
| I.48 | amino | propyl | n-pentyl |
| I.49 | methyl | propyl | n-hexyl |
| I.50 | amino | propyl | n-hexyl |
| I.51 | methyl | isopropyl | isopropyl |
| I.52 | amino | isopropyl | isopropyl |
| I.53 | methyl | isopropyl | butyl |
| I.54 | amino | isopropyl | butyl |
| I.55 | methyl | isopropyl | n-pentyl |
| I.56 | amino | isopropyl | n-pentyl |
| I.57 | methyl | isopropyl | n-hexyl |
| I.58 | amino | isopropyl | n-hexyl |
| I.59 | methyl | butyl | butyl |
| I.60 | amino | butyl | butyl |
| I.61 | methyl | butyl | n-pentyl |
| I.62 | amino | butyl | n-pentyl |
| I.63 | methyl | butyl | n-hexyl |
| I.64 | amino | butyl | n-hexyl |
| I.65 | methyl | n-pentyl | n-pentyl |
| I.66 | amino | n-pentyl | n-pentyl |
| I.67 | methyl | n-pentyl | n-hexyl |
| I.68 | amino | n-pentyl | n-hexyl |
| I.69 | methyl | n-hexyl | n-hexyl |
| I.70 | amino | n-hexyl | n-hexyl |
| I.71 | methyl | —(CH$_2$)$_4$— | |
| I.72 | amino | —(CH$_2$)$_4$— | |
| I.73 | methyl | —(CH$_2$)$_2$—O—(CH$_2$)$_2$— | |
| I.74 | amino | —(CH$_2$)$_2$—O—(CH$_2$)$_2$— | |

Among the compositions according to the invention, preference is given to those which comprise at least one herbicide B selected from groups b1) to b7), b9) to b11), b13) or b14), preferably in combination with a 3-phenyluracil of the formula Ia or Ib.

Among the compositions according to the invention, particular preference is given to those which comprise at least one herbicide B selected from groups b1), b2), b5), b6), b7), b9), b10), b13) and b14), in particular selected from groups b2), b5), b6), b7), b9) and b10), preferably in combination with a 3-phenyluracil of the formula Ia or Ib.

Preferred herbicides B of groups b1) to b15) are the compounds listed below:

b1) clodinafop, cyhalofop, diclofop, fenoxaprop, fenoxaprop-P, fluazifop, fluazifop-P, haloxyfop, haloxyfop-P, metamifop, quizalofop, quizalofop-P, alloxydim, butroxydim, clethodim, cloproxydim, cycloxydim, profoxydim, sethoxydim, tepraloxydim, tralkoxydim;

b2) amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, propoxycarbazone, flucarbazone, imazamethabenz, imazamox, imazapic, imazapyr, imazaquin, imazethapyr, cloransulam, diclosulam, florasulam, flumetsulam, metosulam, penoxsulam, bispyribac, pyribenzoxim, pyriftalid, pyrithiobac, pyriminobac;

b3) atrazine, cyanazine, simazine, terbuthylazine, hexazinone, metamitron, metribuzin, amicarbazone, chloridazon, chlorbromuron, chlorotoluron, diuron, isoproturon, linuron, methabenzthiazuron, propanil, bromoxynil, ioxynil, bentazone, pyridate, difenzoquat, diquat, paraquat;

b4) acifluorfen, fluoroglycofen, halosafen, lactofen, oxyfluorfen, fluazolate, pyraflufen, cinidon-ethyl, flumiclorac, flumioxazin, fluthiacet, oxadiazon, oxadiargyl, azafenidin, carfentrazone, sulfentrazone, pentoxazone, benzfendizone, butafenacil, pyraclonil, profluazol, flufenpyr, nipyraclofen;

b5) norflurazon, diflufenican, picolinafen, beflubutamid, fluridone, flurochloridone, flurtamone, mesotrione, sulcotrione, isoxachlortole, isoxaflutole, benzofenap, pyrazolynate, pyrazoxyfen, benzobicyclon, clomazone, 4-(3-trifluoromethylphenoxy)-2-(4-trifluoromethylphenyl)-pyrimnidine, [2-chloro-3-(4,5-dihydro-3-isoxazolyl)-4-(methylsulfonyl)phenyl](5-hydroxy-1-methyl-1H-pyrazol-4-yl)methanone, [3-(4,5-dihydro-3-isoxazolyl)-2-methyl-4-(methylsulfonyl)phenyl](5-hydroxy-1-methyl-IH-pyrazol-4-yl)methanone, [2-chloro-3-(3-methyl-5-isoxazolyl)-4-(methylsulfonyl)phenyl](5-hydroxy-1-methyl-1H-pyrazol-4-yl)methanone and (5-hydroxy-1-methyl-1H-pyrazol-4-yl) [2-methyl-3-(3-methyl-5-isoxazolyl)-4-(methylsulfonyl)phenyl]methanone;

b6) glyphosate;

b7) glufosinate;

b9) benfluralin, butralin, dinitramine, ethalfluralin, oryzalin, pendimethalin, trifluralin, propyzamide;

b10) acetochlor, alachlor, butachlor, dimethenamid, dimethenamid-P, metazachlor, metolachlor, S-metolachlor, pethoxamid, pretilachlor, propachlor, propisochlor, thenylchlor, flufenacet, mefenacet, fentrazamide, cafenstrole, indanofan;

b11) dichlobenil, chlorthiamid, isoxaben, flupoxam;

b13) 2,4-D, 2,4-DB, dichlorprop, dichlorprop-P, MCPA, MCPB, mecoprop, mecoprop-P, dicamba, quinclorac, quinmerac, clopyralid, fluroxypyr, picloram, triclopyr, benazolin;

b14) diflufenzopyr;

b15) bromobutide, cinmethylin, methyldymron, oxaziclomefone, triaziflam;

and their agriculturally acceptable salts and, in the case of compounds having a carboxyl group, also their agriculturally acceptable derivatives.

Among the compositions which comprise at least one bleacher herbicide b5) and are particularly preferred according to the invention, one embodiment of the invention relates to those compositions which, as bleacher herbicide b5) comprise a compound of the formula II, preferably in combination with a 3-phenyluracil of the formula Ia or Ib. In this embodiment, preference is given to those compositions which comprise a compound of the formula II in which the variables $R^8$ to $R^{13}$ independently of one another and particularly preferably together have the following meanings:

$R^8$ is halogen, $C_1$-$C_4$-alkyl, $C_1$-$C_4$-alkylthio, $C_1$-$C_4$-alkylsulfinyl or $C_1$-$C_4$-alkylsulfonyl, in particular halogen or $C_1$-$C_4$-alkyl and especially methyl or chlorine;

$R^9$ is a heterocyclic radical selected from the group consisting of: isoxazo-1-3-yl, isoxazo-1-5-yl and 4,5-dihydroisoxazo-1-3-yl, where the three radicals mentioned may be unsubstituted or mono- or disubstituted by halogen, $C_1$-$C_4$-alkyl, c1-$C_4$-alkoxy or $C_1$-$C_4$-haloalkyl, in particular isoxazo-1-5-yl or 4,5-dihydroisoxazo-1-3-yl, which may be substituted in the above manner, preferably by one or two $C_1$-$C_4$-alkyl, in particular methyl, groups, for example 4,5-dihydroisoxazol-3-yl or 3-methylisoxazol-5-yl;

$R^{10}$ is halogen, $C_1$-$C_4$-alkyl, $C_1$-$C_4$-alkylthio, $C_1$-$C_4$-alkylsulfinyl or $C_1$-$C_4$-alkylsulfonyl, in particular $C_1$-$C_4$-alkylsulfonyl and particularly preferably methylsulfonyl;

$R^{11}$ is hydrogen;

$R^{12}$ is $C_1$-$C_4$-alkyl;

$R^{13}$ is hydrogen or. $C_1$-$C_4$-alkyl, in particular hydrogen.

Among these, preference is given to those compositions which comprise the compounds II in combination with a 3-phenyluracil of the formula Ia or Ib.

As active compounds C, the compositions according to the invention particularly preferably comprise at least one of the compounds listed below: benoxacor, cloquintocet, dichlormid, fenchlorazole, fenclorim, fluxofenim, furilazole, isoxadifen, mefenpyr, 2,2,5-trimethyl-3-(dichloracetyl)-1,3-oxazolidine, 4-(dichloroacetyl)-1-oxa-4-azaspiro[4.5]decane and oxabetrinil and/or an agriculturally acceptable salt thereof and/or, in the case of compounds having a COOH group, an agriculturally acceptable derivative.

Particular preference is given to those binary and ternary compositions which comprise at least one 3-phenyluracil of the formula I as active compound-A and at least one herbicide selected from classes b1) to b15) and, if appropriate, one or more safeners C.

Here and below, the term "binary compositions" includes compositions which comprise one or more, for example 2 or 3, active compounds A and one or more, for example 2 or 3, herbicides B or one or more, for example 2 or 3, safeners C. Correspondingly, the term "ternary compositions" includes compositions which comprise one or more, for example 2 or 3, active compounds A, one or more, for example 2 or 3, herbicides B and one or more, for example 2 or 3, safeners C.

In binary compositions which comprise at least one 3-phenyluracil of the formula I as component A and at least one herbicide B, the weight ratio of the active compounds A:B is usually in the range from 1:500 to 10:1, preferably in the range from 1:100 to 10:1, in particular in the range from 1:50 to 10:1 and particularly preferably in the range from 1:25 to 5:1.

In binary compositions which comprise at least one 3-phenyluracil of the formula I and at least one safener C, the weight ratio of the active compounds A:C is usually in the range from 1:100 to 10:1, preferably from 1:50 to 10:1 and in particular in the range from 1:25 to 5:1.

In ternary compositions which comprise both a 3-phenyluracil I as component A, at least one herbicide B and at least one safener C, the relative weight ratios of the components A:B:C are usually in the range from 10:1:1 to 1:500:10, preferably from 10:1:1 to 1:100:10, in particular from 10:1:1 to 1:50:1 and particularly preferably from 5:1:1 to 1:25:5. In these ternary compositions, the weight ratio of herbicide B to safener C is preferably in the range from 50:1 to 1:10.

In a particularly preferred embodiment of the invention, preference is given to those compositions of the invention which comprise a 3-phenyluracil of the formula I, especially of formulae Ia or Ib, in combination with at least one and especially exactly one herbicidally active compound of the group b1), in particular selected from the group consisting of clodinafop, diclofop, fenoxaprop, fenoxaprop-P, profoxydim, sethoxydim, tepraloxydim and tralkoxydim and, if desired, a safener C), in particular selected from the group consisting of fenclorazole, cloquintocet, isoxadifen and mefenpyr.

In another particularly preferred embodiment of the invention, preference is given to those compositions of the invention which comprise a 3-phenyluracil of the formula I, especially of formulae Ia or Ib, in combination with at least one and especially exactly one herbicidally active compound of the group b2), in particular selected from the group consisting of amidosulfuron, chlorsulfuron, foramsulfuron, iodosulfuron, mesosulfuron, metsulfuron, nicosulfuron, primisulfuron, prosulfuron, rimsulfuron, sulfosulfuron, tritosulfuron, propoxycarbazone, flucarbazone, imazamethabenz, imazamox, imazapic, imazapyr, imazaquin, imazethapyr, metosulam, diclosulam, florasulam, penoxsulam, pyriftalid and pyriminobac and, if desired, a safener C), in particular selected from the group consisting of furilazole, fenclorazole, cloquintocet, isoxadifen and mefenpyr.

In another particularly preferred embodiment of the invention, preference is given to those compositions of the invention which comprise a 3-phenyluracil of the formula I, especially of formulae Ia or Ib, in combination with at least one and especially exactly one herbicidally active compound of the group b3), in particular selected from the group consisting of atrazine, cyanazine, terbuthylazine, amicarbazone, chlorotoluron, diuron, isoproturon, methabenzthiazuron, propanil, bromoxynil, ioxynil and paraquat and, if desired, a safener C), in particular selected from the group consisting of furilazole, fenclorazole, cloquintocet, isoxadifen and mefenpyr.

In another particularly preferred embodiment of the invention, preference is given to those compositions of the invention which comprise a 3-phenyluracil of the formula I, especially of formulae Ia or Ib, in combination with at least one and especially exactly one herbicidally active compound of the group b5), in particular selected from the group consisting of diflufenican, picolinafen, mesotrione, sulcotrione, isoxaflutole, 4-(3-trifluoromethylphenoxy)-2-($^4$-trifluoromethylphenyl)pyrimidine, [2-chloro-3-(4,5-dihydro-3-isoxazolyl)-4-(methylsulfonyl)phenyl](5-hydroxy-1-methyl-1H-pyrazol-4-yl)methanone and [3-(4,5-dihydro-3-isoxazolyl)-2-methyl-4-(methylsulfonyl)phenyl](5-hydroxy-1-methyl-1H-pyrazol-4-yl)methanone and, if desired, a safener C), in particular selected from the group consisting of furilazole, fenclorazole, cloquintocet, ioxadifen and mefenpyr.

In another particularly preferred embodiment of the invention, preference is given to those compositions of the invention which comprise a 3-phenyluracil of the formula I, especially of formulae Ia or Ib, in combination with at least one and especially exactly one herbicidally active compound of the group b6), in particular glyphosate and, if desired, a safener C), in particular selected from the group consisting of furilazole, fenclorazole, cloquintocet, isoxadifen and mefenpyr.

In another particularly preferred embodiment of the invention, preference is given to those compositions of the invention which comprise a 3-phenyluracil of the formula I, especially of formulae Ia or Ib, in combination with at least one and especially exactly one herbicidally active compound of the group b7), in particular glufosinate and, if desired, a safener C), in particular selected from the group consisting of furilazole, fenclorazole, cloquintocet, isoxadifen and mefenpyr.

In another particularly preferred embodiment of the invention, preference is given to those compositions of the invention which comprise a 3-phenyluracil of the formula I, especially of formulae Ia or Ib, in combination with at least one and especially exactly one herbicidally active compound of the group b9), in particular pendimethalin and, if desired, a safener C), in particular selected from the group consisting of furilazole, fenclorazole, cloquintocet, isoxadifen and mefenpyr.

In another particularly preferred embodiment of the invention, preference is given to those compositions of the invention which comprise a 3-phenyluracil of the formula I, especially of formulae Ia or Ib, in combination with at least one and especially exactly one herbicidally active compound of the group b10), in particular selected from the group consisting of acetochlor, butachlor, dimethenamid, dimethenamid-P, metolachlor, S-metolachlor, pethoxamid, pretilachlor, flufenacet, mefenacet and fentrazamide and, if desired, a Safener C), in particular selected from the group consisting of 2,2,5-trimethyl-3-(dichloroacetyl)-1,3-oxazolidine, dichlormid, furilazole, oxabetrinil, fluxofenim, benoxacor, fenclorim and 4-(dichloroacetyl)-1-oxa-4-azaspiro[4.5]decane.

In another particularly preferred embodiment of the invention, preference is given to those compositions of the invention which comprise a 3-phenyluracil of the formula I, especially of formulae Ia or Ib, in combination with at least one and especially exactly one herbicidally active compound of the group b13), in particular selected from the group consisting of 2,4-D, dichlorprop, dichlorprop-P, mecoprop, MCPA, mecoprop-P, dicamba, quinclorac and quinmerac and, if desired, a safener C), in particular selected from the group consisting of furilazole, fenclorazole, cloquintocet, isoxadifen and mefenpyr.

In another particularly preferred embodiment of the invention, preference is given to those compositions of the invention which comprise a 3-phenyluracil of the formula I, especially of formulae Ia or Ib, in combination with at least one and especially exactly one herbicidally active compound of the group b14), in particular diflufenzopyr and, if desired, a safener C), in particular selected from the group consisting of furilazole, fenclorazole, cloquintocet, isoxadifen and mefenpyr.

In another particularly preferred embodiment of the invention, preference is given to those compositions of the invention which comprise a 3-phenyluracil of the formula I, especially of formulae Ia or Ib, in combination with at least one and especially exactly one herbicidally active compound of the group b15), in particular selected from the group consisting of cinmethylin, oxaziclomefone and triaziflam and, if desired, a safener C), in particular selected from the group consisting of furilazole, fenclorazole, cloquintocet, isoxadifen and mefenpyr.

In another particularly preferred embodiment of the invention, preference is given to those compositions of the invention which comprise a 3-phenyluracil of the formula I, especially of formulae Ia or Ib, in combination with at least one and especially exactly one safener C), in particular selected from the group consisting of furilazole, fenclorazole, cloquintocet, isoxadifen and mefenpyr.

In another particularly preferred embodiment of the invention, preference is given to those compositions of the invention which comprise a 3-phenyluracil of the formula I, especially of formulae Ia or Ib, in combination with at least one and especially exactly one safener C), in particular selected from the group consisting of 2,2,5-trimethyl-3-(dichloroacetyl)-1,3-oxazolidine, dichlormid, furilazole, oxabetrinil, fluxofenim, benoxacor, fenclorim and 4-(dichloroacetyl)-1-oxa-4-azaspiro[4.5]decane.

Among the compositions according to the invention, particular preference is especially given to those compositions of the invention which comprise a 3-phenyluracil of the formula I, especially of formulae Ia or Ib, in combination with at least one and especially exactly one herbicidally active compound selected from the group consisting of tralkoxydim, profoxydim, fenoxaprop, fenoxaprop-P, imazamox, imazethapyr, nicosulfuron, atrazine, diuron, isoproturon, paraquat, cinidon-ethyl, picolinafen, sulcotrione, glyphosate, glufosinate, pendimethalin, dimethenamid, dimethenamid-P, acetochlor, metolachlor, S-metolachlor, isoxaben, dichlorprop, dichlorprop-P, dicamba, 2,4-D, diflufenzopyr and/or a safener C) selected from the group consisting of mefenpyr and benoxacor.

In the preferred or especially preferred compositions described above the herbicides B) as well as the safeners C) can be used in the form of their agriculturally acceptable salts or in the form of an agriculturally acceptable derivative thereof as described above. The weight ratios of the individual components in the compositions are within the limits stated above. Among the especially preferred compositions, particular preference is given to those compositions of the invention in which the variables $R^1$ to $R^7$ have the preferred meanings, especially the particularly preferred meanings. Particular preference is given to 3-phenyluracil of the formula Ia or Ib as defined above.

Preference is given, for example, to those compositions which, as active compound A), comprise the phenyluracil I.1 and, as further active compound, the substances listed in one row of Table 2 (compositions 1.1 to 1.346). The weight ratios of the individual components in the compositions 1.1 to 1.346 are within the stated limits, in the case of binary mixtures of phenyluracil I.1 and herbicide B) for example 1:1, in the case of binary mixtures of phenyluracil I.1 and safener C for example 1:1 and in the case of ternary mixtures of phenyluracil I.1, herbicide B and safener C for example 1:1:1, 2:1:1, 1:2:1, 1:5:1 or 1:5:2.

TABLE 2

| Composition No. | Herbicide B) | Safener C) |
| --- | --- | --- |
| 1.1 | clodinafop | — |
| 1.2 | clodinafop | cloquintocet |
| 1.3 | clodinafop | fenchlorazole |
| 1.4 | clodinafop | isoxadifen |
| 1.5 | clodinafop | mefenpyr |
| 1.6 | cyhalofop | — |
| 1.7 | cyhalofop | cloquintocet |
| 1.8 | cyhalofop | fenchlorazole |
| 1.9 | cyhalofop | isoxadifen |
| 1.10 | cyhalofop | mefenpyr |
| 1.11 | diclofop | — |
| 1.12 | diclofop | cloquintocet |
| 1.13 | diclofop | fenchlorazole |
| 1.14 | diclofop | isoxadifen |
| 1.15 | diclofop | mefenpyr |
| 1.16 | fenoxaprop | — |
| 1.17 | fenoxaprop | cloquintocet |
| 1.18 | fenoxaprop | fenchlorazole |
| 1.19 | fenoxaprop | isoxadifen |
| 1.20 | fenoxaprop | mefenpyr |
| 1.21 | fenoxaprop-P | — |
| 1.22 | fenoxaprop-P | cloquintocet |
| 1.23 | fenoxaprop-P | fenchlorazole |
| 1.24 | fenoxaprop-P | isoxadifen |
| 1.25 | fenoxaprop-P | mefenpyr |
| 1.26 | fluazifop | — |
| 1.27 | fluazifop | cloquintocet |
| 1.28 | fluazifop | fenchlorazole |
| 1.29 | fluazifop | isoxadifen |
| 1.30 | fluazifop | mefenpyr |
| 1.31 | fluazifop-P | — |
| 1.32 | fluazifop-P | cloquintocet |
| 1.33 | fluazifop-P | fenchlorazole |
| 1.34 | fluazifop-P | isoxadifen |
| 1.35 | fluazifop-P | mefenpyr |
| 1.36 | haloxyfop | — |
| 1.37 | haloxyfop | cloquintocet |
| 1.38 | haloxyfop | fenchlorazole |
| 1.39 | haloxyfop | isoxadifen |
| 1.40 | haloxyfop | mefenpyr |
| 1.41 | haloxyfop-P | — |
| 1.42 | haloxyfop-P | cloquintocet |
| 1.43 | haloxyfop-P | fenchlorazole |
| 1.44 | tialoxyfop-P | isoxadifen |
| 1.45 | tialoxyfop-P | mefenpyr |
| 1.46 | quizalofop | — |
| 1.47 | quizalofop | cloquintocet |
| 1.48 | quizalofop | fenchlorazole |
| 1.49 | quizalofop | isoxadifen |
| 1.50 | quizalofop | mefenpyr |
| 1.51 | quizalofop-P | — |
| 1.52 | quizalofop-P | cloquintocet |
| 1.53 | quizalofop-P | fenchlorazole |
| 1.54 | quizalofop-P | isoxadifen |
| 1.55 | quizalofop-P | mefenpyr |
| 1.56 | alloxydim | — |
| 1.57 | butroxydim | — |
| 1.58 | clethodim | — |
| 1.59 | cloproxydim | — |
| 1.60 | cycloxydim | — |
| 1.61 | profoxydim | — |
| 1.62 | sethoxydim | — |
| 1.63 | tepraloxydim | — |
| 1.64 | tralkoxydim | — |
| 1.65 | amidosulfuron | — |
| 1.66 | amidosulfuron | cloquintocet |
| 1.67 | amidosulfuron | fenchlorazole |
| 1.68 | amidosulfuron | isoxadifen |
| 1.69 | amidosulfuron | mefenpyr |
| 1.70 | amidosulfuron | furilazole |
| 1.71 | azimsulfuron | — |
| 1.72 | bensulfuron | — |
| 1.73 | chlorimuron | — |
| 1.74 | chlorsulfuron | — |
| 1.75 | cinosulfuron | — |
| 1.76 | cyclosulfamuron | — |
| 1.77 | ethametsulfuron | — |
| 1.78 | ethoxysulfuron | — |
| 1.79 | flazasulfuron | — |
| 1.80 | flupyrsulfuron | — |
| 1.81 | foramsulfuron | — |
| 1.82 | foramsulfuron | cloquintocet |
| 1.83 | foramsulfuron | fenchlorazole |
| 1.84 | foramsulfuron | isoxadifen |
| 1.85 | foramsulfuron | mefenpyr |
| 1.86 | foramsulfuron | furilazole |
| 1.87 | halosulfuron | — |
| 1.88 | halosulfuron | cloquintocet |
| 1.89 | halosulfuron | fenchlorazole |
| 1.90 | halosulfuron | isoxadifen |
| 1.91 | halosulfuron | mefenpyr |
| 1.92 | halosulfuron | furilazole |
| 1.93 | imazosulfuron | — |
| 1.94 | iodosulfuron | — |
| 1.95 | iodosulfuron | cloquintocet |
| 1.96 | iodosulfuron | fenchlorazole |
| 1.97 | iodosulfuron | isoxadifen |
| 1.98 | iodosulfuron | mefenpyr |
| 1.99 | iodosulfuron | furilazole |
| 1.100 | mesosulfuron | — |
| 1.101 | mesosulfuron | cloquintocet |
| 1.102 | mesosulfuron | fenchlorazole |
| 1.103 | mesosulfuron | isoxadifen |
| 1.104 | mesosulfuron | mefenpyr |
| 1.105 | mesosulfuron | furilazole |
| 1.106 | metsulfuron | — |
| 1.107 | nicosulfuron | — |
| 1.108 | oxasulfuron | — |
| 1.109 | primisulfuron | — |
| 1.110 | prosulfuron | — |
| 1.111 | pyrazosulfuron | — |
| 1.112 | rimsulfuron | — |
| 1.113 | sulfometuron | — |
| 1.114 | sulfosulfuron | — |
| 1.115 | thifensulfuron | — |
| 1.116 | triasulfuron | — |
| 1.117 | tribenuron | — |

TABLE 2-continued

| Composition No. | Herbicide B) | Safener C) |
|---|---|---|
| 1.118 | trifloxysulfuron | — |
| 1.119 | triflusulfuron | — |
| 1.120 | tritosulfurone | — |
| 1.121 | propoxycarbazone | — |
| 1.122 | flucarbazone | — |
| 1.123 | imazamethabenz | — |
| 1.124 | imazamox | — |
| 1.125 | imazapic | — |
| 1.126 | imazapyr | — |
| 1.127 | imazaquin | — |
| 1.128 | imazethapyr | — |
| 1.129 | cloransulam | — |
| 1.130 | diclosulam | — |
| 1.131 | florasulam | — |
| 1.132 | flumetsulam | — |
| 1.133 | metosulam | — |
| 1.134 | penoxsulam | — |
| 1.135 | bispyribac | — |
| 1.136 | pyribenzoxim | — |
| 1.137 | pyriftalid | — |
| 1.138 | pyrithiobac | — |
| 1.139 | pyriminobac | — |
| 1.140 | atrazine | — |
| 1.141 | cyanazine | — |
| 1.142 | simazine | — |
| 1.143 | terbuthylazine | — |
| 1.144 | hexazinone | — |
| 1.145 | metamitron | — |
| 1.146 | metribuzin | — |
| 1.147 | amicarbazone | — |
| 1.148 | chloridazon | — |
| 1.149 | chlorbromuron | — |
| 1.150 | chlorotoluron | — |
| 1.151 | diuron | — |
| 1.152 | isoproturon | — |
| 1.153 | linuron | — |
| 1.154 | methabenzthiazuron | — |
| 1.155 | propanil | — |
| 1.156 | bromoxynil | — |
| 1.157 | ioxynil | — |
| 1.158 | bentazone | — |
| 1.159 | pyridate | — |
| 1.160 | difenzoquat | — |
| 1.161 | diquat | — |
| 1.162 | paraquat | — |
| 1.163 | acifluorfen | — |
| 1.164 | fluoroglycofen | — |
| 1.165 | halosafen | — |
| 1.166 | lactofen | — |
| 1.167 | oxyfluorfen | — |
| 1.168 | fluazolate | — |
| 1.169 | pyraflufen | — |
| 1.170 | cinidon-ethyl | — |
| 1.171 | flumiclorac | — |
| 1.172 | flumioxazin | — |
| 1.173 | fluthiacet | — |
| 1.174 | oxadiazon | — |
| 1.175 | oxadiargyl | — |
| 1.176 | azafenidin | — |
| 1.177 | carfentrazone | — |
| 1.178 | sulfentrazone | — |
| 1.179 | pentoxazone | — |
| 1.180 | benzfendizone | — |
| 1.181 | butafenacil | — |
| 1.182 | pyraclonil | — |
| 1.183 | profluazol | — |
| 1.184 | flufenpyr | — |
| 1.185 | nipyraclofen | — |
| 1.186 | norflurazon | — |
| 1.187 | diflufenican | — |
| 1.188 | picolinafen | — |
| 1.189 | beflubutamid | — |
| 1.190 | fluridone | — |
| 1.191 | flurochloridone | — |
| 1.192 | flurtamone | — |
| 1.193 | mesotrione | — |
| 1.194 | sulcotrione | — |
| 1.195 | isoxachlortole | — |
| 1.196 | isoxaflutole | — |
| 1.197 | benzofenap | — |
| 1.198 | pyrazolynate | — |
| 1.199 | pyrazoxyfen | — |
| 1.200 | benzobicyclon | — |
| 1.201 | clomazone | — |
| 1.202 | [2-chloro-3-(4,5-dihydro-3-isoxazolyl)-4-(methylsulfonyl)phenyl](5-hydroxy-1-methyl-1H-pyrazol-4-yl)methanone | — |
| 1.203 | [3-(4,5-dihydro-3-isoxazolyl)-2-methyl-4-(methylsulfonyl)phenyl](5-hydroxy-1-methyl-1H-pyrazol-4-yl)methanone | — |
| 1.204 | [2-chloro-3-(3-methyl-5-isoxazolyl)-4-(methylsulfonyl)phenyl](5-hydroxy-1-methyl-1H-pyrazol-4-yl)methanone | — |
| 1.205 | (5-hydroxy-1-methyl-1H-pyrazol-4-yl)[2-methyl-3-(3-methyl-5-isoxazolyl)-4-(methylsulfonyl)phenyl]methanone | — |
| 1.206 | glyphosate | — |
| 1.207 | glufosinate | — |
| 1.208 | benfluralin | — |
| 1.209 | butralin | — |
| 1.210 | dinitramine | — |
| 1.211 | ethalfluralin | — |
| 1.212 | oryzalin | — |
| 1.213 | pendimethalin | — |
| 1.214 | trifluralin | — |
| 1.215 | propyzamide | — |
| 1.216 | acetochlor | — |
| 1.217 | acetochlor | dichlormid |
| 1.218 | acetochlor | furilazole |
| 1.219 | acetochlor | oxabetrinil |
| 1.220 | acetochlor | fluxofenim |
| 1.221 | acetochlor | benoxacor |
| 1.222 | acetochlor | fenclorim |
| 1.223 | alachlor | — |
| 1.224 | butachlor | — |
| 1.225 | butachlor | dichlormid |
| 1.226 | butachlor | furilazole |
| 1.227 | butachlor | oxabetrinil |
| 1.228 | butachlor | fluxofenim |
| 1.229 | butachlor | benoxacor |
| 1.230 | butachlor | fenclorim |
| 1.231 | dimethenamid | — |
| 1.232 | dimethenamid | dichlormid |
| 1.233 | dimethenamid | furilazole |
| 1.234 | dimethenamid | oxabetrinil |
| 1.235 | dimethenamid | fluxofenim |
| 1.236 | dimethenamid | benoxacor |
| 1.237 | dimethenamid | fenclorim |
| 1.238 | dimethenamid-P | — |
| 1.239 | dimethenamid-P | dichlormid |
| 1.240 | dimethenamid-P | furilazole |
| 1.241 | dimethenamid-P | oxabetrinil |
| 1.242 | dimethenamid-P | fluxofenim |
| 1.243 | dimethenamid-P | benoxacor |
| 1.244 | dimethenamid-P | fenclorim |
| 1.245 | metazachlor | — |
| 1.246 | metolachlor | — |
| 1.247 | metolachlor | dichlormid |
| 1.248 | metolachlor | furilazole |
| 1.249 | metolachlor | oxabetrinil |
| 1.250 | metolachlor | fluxofenim |
| 1.251 | metolachlor | benoxacor |
| 1.252 | metolachlor | fenclorim |
| 1.253 | S-metolachlor | — |
| 1.254 | S-metolachlor | dichlormid |
| 1.255 | S-metolachlor | furilazole |

TABLE 2-continued

| Composition No. | Herbicide B) | Safener C) |
|---|---|---|
| 1.256 | S-metolachlor | oxabetrinil |
| 1.257 | S-metolachlor | fluxofenim |
| 1.258 | S-metolachlor | benoxacor |
| 1.259 | S-metolachlor | fenclorim |
| 1.260 | pethoxamid | — |
| 1.261 | pretilachlor | — |
| 1.262 | pretilachlor | dichlormid |
| 1.263 | pretilachlor | furilazole |
| 1.264 | pretilachlor | oxabetrinil |
| 1.265 | pretilachlor | fluxofenim |
| 1.266 | pretilachlor | benoxacor |
| 1.267 | pretilachlor | fenclorim |
| 1.268 | flupoxam | — |
| 1.269 | propachlor | — |
| 1.270 | propisochlor | — |
| 1.271 | thenylchlor | — |
| 1.272 | flufenacet | — |
| 1.273 | mefenacet | — |
| 1.274 | fentrazamide | — |
| 1.275 | cafenstrole | — |
| 1.276 | indanofan | — |
| 1.277 | dichlobenil | — |
| 1.278 | chlorthiamid | — |
| 1.279 | isoxaben | — |
| 1.280 | 2,4-D | — |
| 1.281 | 2,4-DB | — |
| 1.282 | dichlorprop | — |
| 1.283 | dichlorprop-P | — |
| 1.284 | MCPA | — |
| 1.285 | MCPB | — |
| 1.286 | mecoprop | — |
| 1.287 | mecoprop-P | — |
| 1.288 | dicamba | — |
| 1.289 | quinclorac | — |
| 1.290 | quinmerac | — |
| 1.291 | clopyralid | — |
| 1.292 | fluroxypyr | — |
| 1.293 | picloram | — |
| 1.294 | triclopyr | — |
| 1.295 | benazolin | — |
| 1.296 | diflufenzopyr | — |
| 1.297 | bromobutide | — |
| 1.298 | cinmethylin | — |
| 1.299 | methyldymron | — |
| 1.300 | oxaziclomefone | — |
| 1.301 | triaziflam | — |
| 1.302 | — | benoxacor |
| 1.303 | — | cloquintocet |
| 1.304 | — | cyometrinil |
| 1.305 | — | dichlormid |
| 1.306 | — | dicyclonon |
| 1.307 | — | dietholate |
| 1.308 | — | fenchlorazole |
| 1.309 | — | fenclorim |
| 1.310 | — | flurazole |
| 1.311 | — | fluxofenim |
| 1.312 | — | furilazole |
| 1.313 | — | isoxadifen |
| 1.314 | — | mefenpyr |
| 1.315 | — | mephenate |
| 1.316 | — | naphthalic anhydride |
| 1.317 | — | oxabetrinil |
| 1.318 | — | 2,2,5-trimethyl-3-(dichloroacetyl)oxazolidine |
| 1.319 | 4-(3-trifluoromethylphenoxy)-2-(4-trifluoromethylphenyl)pyrimidine | — |
| 1.320 | acetochlor | 2,2,5-trimethyl-3-(dichloro-acetyl)-1,3-oxa-zolidine |
| 1.321 | butachlor | 2,2,5-trimethyl-3-(dichloro-acetyl)-1,3-oxa-zolidine |
| 1.322 | dimethenamid | 2,2,5-trimethyl-3-(dichloro-acetyl)-1,3-oxa-zolidine |
| 1.323 | dimethenamid-P | 2,2,5-trimethyl-3-(dichloro-acetyl)-1,3-oxa-zolidine |
| 1.324 | metolachlor | 2,2,5-trimethyl-3-(dichloro-acetyl)-1,3-oxa-zolidine |
| 1.325 | S-metolachlor | 2,2,5-trimethyl-3-(dichloro-acetyl)-1,3-oxa-zolidine |
| 1.326 | pretilachlor | 2,2,5-trimethyl-3-(dichloro-acetyl)-1,3-oxa-zolidine |
| 1.327 | pethoxamid | 2,2,5-trimethyl-3-(dichloro-acetyl)-1,3-oxa-zolidine |
| 1.328 | pethoxamid | dichlormid |
| 1.329 | pethoxamid | furilazole |
| 1.330 | pethoxamid | oxabetrinil |
| 1.331 | pethoxamid | fluxofenim |
| 1.332 | pethoxamid | benoxacor |
| 1.333 | pethoxamid | fenclorim |
| 1.334 | pethoxamid | 4-(dichloro-acetyl)-1-oxa-4-azaspiro[4.5]-decane |
| 1.335 | acetochlor | 4-(dichloro-acetyl)-1-oxa-4-azaspiro[4.5]-decane |
| 1.336 | butachlor | 4-(dichloro-acetyl)-1-oxa-4-azaspiro[4.5]-decane |
| 1.337 | dimethenamid | 4-(dichloro-acetyl)-1-oxa-4-azaspiro[4.5]-decane |
| 1.338 | dimethenamid-P | 4-(dichloro-acetyl)-1-oxa-4-azaspiro[4.5]-decane |
| 1.339 | metolachlor | 4-(dichloro-acetyl)-1-oxa-4-azaspiro[4.5]-decane |
| 1.340 | S-metolachlor | 4-(dichloro-acetyl)-1-oxa-4-azaspiro[4.5]-decane |
| 1.341 | pretilachlor | 4-(dichloro-acetyl)-1-oxa-4-azaspiro[4.5]-decane |
| 1.342 | metamifop | — |
| 1.343 | metamifop | cloquintocet |
| 1.344 | metamifop | fenchlorazole |
| 1.345 | metamifop | isoxadifen |
| 1.346 | metamifop | mefenpyr |

If the active compounds mentioned in table 2 have functional groups which can be ionized, they can, of course, also be present in the form of their agriculturally acceptable salts. In the case of acidic active compounds, i.e. active compounds which can be deprotonated, these are in particular the lithium, sodium, potassium, calcium, magnesium, ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)eth-1-ylammonium, di-(2-hydroxyeth-1-yl)ammonium, benzyltrimethylammonium, benzyltriethylammonium or trimethylsulfonium salts. In the case of basic active compounds, i.e. active compounds which can be protonated, these are in particular the chlorides, bromides, sulfates, hydrogen sulfates, methylsulfates, dihydrogen phosphates or hydrogen phosphates of the active compounds mentioned above. If the active compounds mentioned in table 2 have a carboxyl group they can, of course, also be present in the form of agriculturally acceptable derivatives, in particular in the form of their methyl- and dimethylamides, in the form of their anilides or 2-chloroanilides, and also in the form of their methyl, ethyl, propyl, isopropyl, butyl, isobutyl, pentyl, hexyl, isooctyl, methoxyethyl, ethoxyethyl, butoxyethyl or thioethyl esters.

Preference is also given to the compositions 2.1-2.346 which differ from the corresponding compositions 1.1-1.346 only in that the phenyluracil I.1 is replaced by the phenyluracil I.2.

Preference is also given to the compositions 3.1-3.346 which differ from the corresponding compositions 1.1-1.346 only in that the phenyluracil I.1 is replaced by the phenyluracil I.3.

Preference is also given to the compositions 4.1-4.346 which differ from the corresponding compositions 1.1-1.346 only in that the phenyluracil I.1 is replaced by the phenyluracil I.4.

Preference is also given to the compositions 5.1-5.346 which differ from the corresponding compositions 1.1-1.346 only in that the phenyluracil I.1 is replaced by the phenyluracil I.5.

Preference is also given to the compositions 6.1-6.346 which differ from the corresponding compositions 1.1-1.346 only in that the phenyluracil I.1 is replaced by the phenyluracil I.6.

Preference is also given to the compositions 7.1-7.346 which differ from the corresponding compositions 1.1-1.346 only in that the phenyluracil I.1 is replaced by the phenyluracil I.7.

Preference is also given to the compositions 8.1-8.346 which differ from the corresponding compositions 1.1-1.346 only in that the phenyluracil I.1 is replaced by the phenyluracil I.8.

Preference is also given to the compositions 9.1-9.346 which differ from the corresponding compositions 1.1-1.346 only in that the phenyluracil 1.1 is replaced by the phenyluracil I.9.

Preference is also given to the compositions 10.1-10.346 which differ from the corresponding compositions 1.1-1.346 only in that the phenyluracil I.1 is replaced by the phenyluracil I.10.

Preference is also given to the compositions 11.1-11.346 which differ from the corresponding compositions 1.1-1.346 only in that the phenyluracil I.1 is replaced by the phenyluracil I.11.

Preference is also given to the compositions 12.1-12.346 which differ from the corresponding compositions 1.1-1.346 only in that the phenyluracil I.1 is replaced by the phenyluracil I.12.

Preference is also given to the compositions 13.1-13.346 which differ from the corresponding compositions 1.1-1.346 only in that the phenyluracil I.1 is replaced by the phenyluracil I.13.

Preference is also given to the compositions 14.1-14.346 which differ from the corresponding compositions 1.1-1.346 only in that the phenyluracil I.1 is replaced by the phenyluracil I.14.

Preference is also given to the compositions 15.1-15.346 which differ from the corresponding compositions 1.1-1.346 only in that the phenyluracil 1.1 is replaced by the phenyluracil I.15.

Preference is also given to the compositions 16.1-16.346 which differ from the corresponding compositions 1.1-1.346 only in that the phenyluracil I.1 is replaced by the phenyluracil I.16.

Preference is also given to the compositions 17.1-17.346 which differ from the corresponding compositions 1.1-1.346 only in that the phenyluracil I.1 is replaced by the phenyluracil I.17.

Preference is also given to the compositions 18.1-18.346 which differ from the corresponding compositions 1.1-1.346 only in that the phenyluracil 1.1 is replaced by the phenyluracil I.18.

Preference is also given to the compositions 19.1-19.346 which differ from the corresponding compositions 1.1-1.346 only in that the phenyluracil 1.1 is replaced by the phenyluracil I.19.

Preference is also given to the compositions 20.1-20.346 which differ from the corresponding compositions 1.1-1.346 only in that the phenyluracil I.1 is replaced by the phenyluracil I.20.

Preference is also given to the compositions 21.1-21.346 which differ from the corresponding compositions 1.1-1.346 only in that the phenyluracil I.1 is replaced by the phenyluracil i.21.

Preference is also given to the compositions 22.1-22.346 which differ from the corresponding compositions 1.1-1.346 only in that the phenyluracil 1.1 is replaced by the phenyluracil I.22.

Preference is also given to the compositions 23.1-23.346 which differ from the corresponding compositions 1.1-1.346 only in that the phenyluracil I.1 is replaced by the phenyluracil I.23.

Preference is also given to the compositions 24.1-24.346 which differ from the corresponding compositions 1.1-1.346 only in that the phenyluracil I.1 is replaced by the phenyluracil i.24.

Preference is also given to the compositions 25.1-25.346 which differ from the corresponding compositions 1.1-1.346 only in that the phenyluracil 1.1 is replaced by the phenyluracil I.25.

Preference is also given to the compositions 26.1-26.346 which differ from the corresponding compositions 1.1-1.346 only in that the phenyluracil I.1 is replaced by the phenyluracil I.26.

Preference is also given to the compositions 27.1-27.346 which differ from the corresponding compositions 1.1-1.346 only in that the phenyluracil I.1 is replaced by the phenyluracil I.27.

Preference is also given to the compositions 28.1-28.346 which differ from the corresponding compositions 1.1-1.346 only in that the phenyluracil I.1 is replaced by the phenyluracil I.28.

Preference is also given to the compositions 29.1-29.346 which differ from the corresponding compositions 1.1-1.346 only in that the phenyluracil I.1 is replaced by the phenyluracil I.29.

Preference is also given to the compositions 30.1-30.346 which differ from the corresponding compositions 1.1-1.346 only in that the phenyluracil I.1 is replaced by the phenyluracil I.30.

Preference is also given to the compositions 31.1-31.346 which differ from the corresponding compositions 1.1-1.346 only in that the phenyluracil I.1 is replaced by the phenyluracil I.31.

Preference is also given to the compositions 32.1-32.346 which differ from the corresponding compositions 1.1-1.346 only in that the phenyluracil I.1 is replaced by the phenyluracil I.32.

Preference is also given to the compositions 33.1-33.346 which differ from the corresponding compositions 1.1-1.346 only in that the phenyluracil 1.1 is replaced by the phenyluracil I.33.

Preference is also given to the compositions 34.1-34.346 which differ from the corresponding compositions 1.1-1.346 only in that the phenyluracil I.1 is replaced by the phenyluracil I.34.

Preference is also given to the compositions 35.1-35.346 which differ from the corresponding compositions 1.1-1.346 only in that the phenyluracil I.1 is replaced by the phenyluracil I.35.

Preference is also given to the compositions 36.1-36.346 which differ from the corresponding compositions 1.1-1.346 only in that the phenyluracil I.1 is replaced by the phenyluracil I.36.

Preference is also given to the compositions 37.1-37.346 which differ from the corresponding compositions 1.1-1.346 only in that the phenyluracil I.1 is replaced by the phenyluracil I.37.

Preference is also given to the compositions 38.1-38.346 which differ from the corresponding compositions 1.1-1.346 only in that the phenyluracil I.1 is replaced by the phenyluracil I.38.

Preference is also given to the compositions 39.1-39.346 which differ from the corresponding compositions 1.1-1.346 only in that the phenyluracil I.1 is replaced by the phenyluracil 1.39.

Preference is also given to the compositions 40.1-40.346 which differ from the corresponding compositions 1.1-1.346 only in that the phenyluracil I.1 is replaced by the phenyluracil I.40.

Preference is also given to the compositions 41.1-41.346 which differ from the corresponding compositions 1.1-1.346 only in that the phenyluracil I.1 is replaced by the phenyluracil I.41.

Preference is also given to the compositions 42.1-42.346 which differ from the corresponding compositions 1.1-1.346 only in that the phenyluracil I.1 is replaced by the phenyluracil I.42.

Preference is also given to the compositions 43.1-43.346 which differ from the corresponding compositions 1.1-1.346 only in that the phenyluracil I.1 is replaced by the phenyluracil I.43.

Preference is also given to the compositions 44.1-44.346 which differ from the corresponding compositions 1.1-1.346 only in that the phenyluracil 1.1 is replaced by the phenyluracil I.44.

Preference is also given to the compositions 45.1-45.346 which differ from the corresponding compositions 1.1-1.346 only in that the phenyluracil I.1 is replaced by the phenyluracil I.45.

Preference is also given to the compositions 46.1-46.346 which differ from the corresponding compositions 1.1-1.346 only in that the phenyluracil I.1 is replaced by the phenyluracil I.46.

Preference is also given to the compositions 47.1-47.346 which differ from the corresponding compositions 1.1-1.346 only in that the phenyluracil I.1 is replaced by the phenyluracil I.47.

Preference is also given to the compositions 48.1-48.346 which differ from the corresponding compositions 1.1-1.346 only in that the phenyluracil I.1 is replaced by the phenyluracil I.48.

Preference is also given to the compositions 49.1-49.346 which differ from the corresponding compositions 1.1-1.346 only in that the phenyluracil I.1 is replaced by the phenyluracil I.49.

Preference is also given to the compositions 50.1-50.346 which differ from the corresponding compositions 1.1-1.346 only in that the phenyluracil I.1 is replaced by the phenyluracil I.50.

Preference is also given to the compositions 51.1-51.346 which differ from the corresponding compositions 1.1-1.346 only in that the phenyluracil I.1 is replaced by the phenyluracil I.51.

Preference is also given to the compositions 52.1-52.346 which differ from the corresponding compositions 1.1-1.346 only in that the phenyluracil I.1 is replaced by the phenyluracil I.52.

Preference is also given to the compositions 53.1-53.346 which differ from the corresponding compositions 1.1-1.346 only in that the phenyluracil I.1 is replaced by the phenyluracil I.53.

Preference is also given to the compositions 54.1-54.346 which differ from the corresponding compositions 1.1-1.346 only in that the phenyluracil I.1 is replaced by the phenyluracil I.54.

Preference is also given to the compositions 55.1-55.346 which differ from the corresponding compositions 1.1-1.346 only in that the phenyluracil I.1 is replaced by the phenyluracil I.55.

Preference is also given to the compositions 56.1-56.346 which differ from the corresponding compositions 1.1-1.346 only in that the phenyluracil I.1 is replaced by the phenyluracil I.56.

Preference is also given to the compositions 57.1-57.346 which differ from the corresponding compositions 1.1-1.346 only in that the phenyluracil I.1 is replaced by the phenyluracil I.57.

Preference is also given to the compositions 58.1-58.346 which differ from the corresponding compositions 1.1-1.346 only in that the phenyluracil I.1 is replaced by the phenyluracil I.58.

Preference is also given to the compositions 58.1-59.346 which differ from the corresponding compositions 1.1-1.346 only in that the phenyluracil I.1 is replaced by the phenyluracil I.59.

Preference is also given to the compositions 60.1-60.346 which differ from the corresponding compositions 1.1-1.346 only in that the phenyluracil I.1 is replaced by the phenyluracil I.60.

Preference is also given to the compositions 61.1-61.346 which differ from the corresponding compositions 1.1-1.346 only in that the phenyluracil I.1 is replaced by the phenyluracil I.61.

Preference is also given to the compositions 62.1-62.346 which differ from the corresponding compositions 1.1-1.346 only in that the phenyluracil I.1 is replaced by the phenyluracil I.62.

Preference is also given to the compositions 63.1-63.346 which differ from the corresponding compositions 1.1-1.346 only in that the phenyluracil I.1 is replaced by the phenyluracil I.63.

Preference is also given to the compositions 64.1-64.346 which differ from the corresponding compositions 1.1-1.346 only in that the phenyluracil I.1 is replaced by the phenyluracil I.64.

Preference is also given to the compositions 65.1-65.346 which differ from the corresponding compositions 1.1-1.346 only in that the phenyluracil I.1 is replaced by the phenyluracil I.65.

Preference is also given to the compositions 66.1-66.346 which differ from the corresponding compositions 1.1-1.346 only in that the phenyluracil I.1 is replaced by the phenyluracil I.66.

Preference is also given to the compositions 67.1-67.346 which differ from the corresponding compositions 1.1-1.346 only in that the phenyluracil I.1 is replaced by the phenyluracil I.67.

Preference is also given to the compositions 68.1-68.346 which differ from the corresponding compositions 1.1-1.346 only in that the phenyluracil I.1 is replaced by the phenyluracil I.68.

Preference is also given to the compositions 69.1-69.346 which differ from the corresponding compositions 1.1-1.346 only in that the phenyluracil I.1 is replaced by the phenyluracil I.69.

Preference is also given to the compositions 70.1-70.346 which differ from the corresponding compositions 1.1-1.346 only in that the phenyluracil I.1 is replaced by the phenyluracil I.70.

Preference is also given to the compositions 71.1-71.346 which differ from the corresponding compositions 1.1-1.346 only in that the phenyluracil I.1 is replaced by the phenyluracil I.71.

Preference is also given to the compositions 72.1-72.346 which differ from the corresponding compositions 1.1-1.346 only in that the phenyluracil I.1 is replaced by the phenyluracil I.72.

Preference is also given to the compositions 73.1-73.346 which differ from the corresponding compositions 1.1-1.346 only in that the phenyluracil I.1 is replaced by the phenyluracil I.73.

Preference is also given to the compositions 74.1-74.346 which differ from the corresponding compositions 1.1-1.346 only in that the phenyluracil I.1 is replaced by the phenyluracil I.74.

The weight ratios of the individual components in the compositions 2.1 to 74-346 are within the limits stated above, in the case of binary mixtures of phenyluracil I.1 and herbicide B) for example 1:1, 1:2 or 1:5, in the case of binary mixtures of phenyluracil I.1 and safener C for example 1:1, 1:2 or 1:5 and in the case of ternary mixtures of phenyluracil I.1, herbicide B and safener C for example 1:1:1, 2:1:1, 1:2:1, 1:5:1 or 1:5:2.

In the ready-to-use preparations, i.e. in the compositions according to the invention in the form of crop protection products, the components A and B and/or C, in suspended, emulsified or dissolved form, can be present formulated jointly or separately. The use forms depend entirely on the intended use.

The compositions according to the invention can be applied, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, broadcasting or watering. The use forms depend on the intended use; in any case, they should ensure the finest possible distribution of the active compounds.

Depending on the form in which the ready-to-use preparations are present in the compositions according to the invention, they comprise one or more liquid or solid carriers, if appropriate surfactants and if appropriate further auxiliaries which are customary for formulating crop protection products. The person skilled in the art is sufficiently familiar with the recipes for such formulations.

The ready-to-use preparations comprise the components A and B and/or C and auxiliaries which are customary for formulating crop protection products, which auxiliaries may also comprise a liquid carrier.

Suitable inert additives with carrier function are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the active compounds A) to C), as such or dissolved in an oil or solvent, can be homogenized in water by means of wetting agent, tackifier, dispersant or emulsifier.

Alternatively, it is possible to prepare concentrates consisting of active substance, wetting agent, tackifier, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, e.g. ligno-, pheno-1-, naphthalene- and dibutylnaphthalenesulfonic acid, and of fatty acids, of alkyl- and alkylarylsulfonates, of alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignosulfite waste liquors or methylcellulose.

Powders, materials for spreading and dusts can be prepared by mixing or concomitant grinding of the active substances with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The concentrations of the active compounds in the ready-to-use preparations can be varied within wide ranges. In general, the formulations comprise from 0.001 to 98% by weight, preferably 0.01 to 95% by weight, of active ingredients. The active ingredients are employed in a purity of from 90% to 100%, preferably 95% to 100% (according to NMR spectrum).

The compounds according to the invention can, for example, be formulated as follows:

I 20 parts by weight of the active compound or active compound mixture in question are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

II 20 parts by weight of the active compound or active compound mixture in question are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

III 20 parts by weight of the active compound or active compound mixture in question are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

IV 20 parts by weight of the active compound or active compound mixture in question are mixed thoroughly with 3 parts by weight of sodium diisobutylnaphthalene-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20 000 parts by weight of water gives a spray mixture which comprises 0.1% by weight of the active ingredient.

V 3 parts by weight of the active compound or active compound mixture in question are mixed with 97 parts by weight of finely divided kaolin. This gives a dust which comprises 3% by weight of the active ingredient.

VI 20 parts by weight of the active compound or active compound mixture in question are mixed intimately with 2 parts by weight of calcium dodecylbenzenesulfonate, 8 parts by weight of fatty alcohol polyglycol ether, 2 parts by weight of the sodium salt of a phenol-urea-formaldehyde condensate and 68 parts by weight of a paraffinic mineral oil. This gives a stable oily dispersion.

VII 1 part by weight of the active compound or active compound mixture in question is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the active compound or active compound mixture in question is dissolved in a mixture composed of 80 parts by weight of cyclohexanone and 20 parts by weight of Wettol® EM 31 (nonionic emulsifier based on ethoxylated castor oil). This gives a stable emulsion concentrate.

The components A and B and/or C can be formulated jointly or separately.

The components A and B and/or C can be applied jointly or separately, simultaneously or successively, before, during or after emergence of the plants.

If the active compounds A and B and/or C are less well tolerated by certain crop plants, it is possible to use application methods in which the herbicidal compositions are sprayed with the aid of sprayers in such a way that the leaves of the sensitive crop plants are as far as possible unaffected, whereas the active compounds reach the leaves of the undesirable plants growing underneath or the uncovered soil surface (post-directed, lay-by).

The required application rate of pure active compound composition, i.e. of A and B and/or C without formulation auxiliary, depends on the composition of the plant stand, on the development stage of the plants, on the climatic conditions of the location where the composition is used and on the application method. In general, the application rate of A and B and/or C is from 0.001 to 3 kg/ha, preferably from 0.005 to 2 kg/ha and in particular from 0.01 to 1 kg/ha of active substance (a.s.).

The required application rates of phenyluracil are generally in the range from 0.1 g/ha to 1 kg/ha and preferably in the range from 1 g/ha to 500 g/ha or from 5 g/ha to 500 g/ha of a.s.

The compositions are applied to the plants mainly by foliar spraying. Application can be carried out by customary spraying techniques using, for example, water as carrier and spray liquor rates of from about 100 to 1000 l/ha (for example from 300 to 400 l/ha). Application of the herbicidal compositions by the low-volume and the ultra-low-volume method is possible, as is their application in the form of microgranules.

The compositions according to the present invention are suitable for controlling common harmful plants in useful plants, in particular in crops such as wheat, barley, oats, corn, soybean, sorghum, rice, oilseed rape, cotton, potatoes, dry beans, groundnuts or in perennial crops. In another embodiment of the invention, they are useful for controlling the whole vegetation, i. e. they act as a total weedkiller. Futhermore, in another emodiment of the present invention, the compositions are useful for controlling undesirable vegetation in forestry.

Moreover, it may be useful to apply the compositions according to the invention jointly as a mixture with other crop protection products, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

The compositions according to the invention can also be used in crop plants which are resistant to one or more herbicides owing to genetic engineering or breeding or which are resistant to attack by insects owing to genetic engineering or breeding. Suitable are for example crop plants which are resistant to herbicidal EPSP synthase inhibitors, such as, for example, glyphosate, to herbicidal glutamine synthase inhibitors, such as, for example, glufosinate, to herbicidal protoporphyrinogen-IX oxidase inhibitors, such as, for example, butafenacil, or to herbicidal ALS inhibitors, such as, for example, imazamethabenz, imazamox, imazapic, imazapyr, imazaquin, imazethapyr, or crop plants which, owing to introduction of the gene for Bt toxin by genetic modification, are resistant to attack by certain insects.

Surprisingly, the compositions according to the invention which comprise at least one phenyluracil of the formula I and at least one herbicide B have better herbicidal activity against harmful plants than would have been expected by the herbicidal activity of the individual compounds. In other words, the joint application of phenyluracil I and herbicide B results in an enhanced activity against harmful plants in the sense of a synergy effect (synergism). For this reason, the mixtures can, based on the individual components, be used at lower application rates to achieve a herbicidal effect comparable to the individual components.

Surprisingly, the compositions according to the invention which, in addition to the phenyluracil I and, if appropriate, the herbicide B comprise an active compound from group C are better tolerated by useful plants than the respective phenyluracil I or the respective mixture of phenyluracil +herbicide B without active compound of group C.

The 3-phenyluracils of the formula I can be prepared by the preparation processes A to D described below, which are the subject of the earlier application PCT/EP 01/04850. With respect to the preparation of individual compounds, reference is made to the examples of PCT/EP 01/04850. Compounds which are not explicitly disclosed in this document can be prepared in an analogous manner.

In the schemes below, Q has the following meaning:

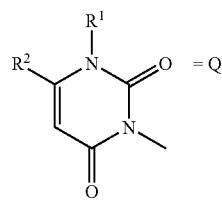

A) Reaction of a benzoic acid derivtive of the formula III in which $R^3$, $R^4$ and Q are as defined above with a sulfonamide IV, if appropriate in the presence of a coupling agent such as N,N-carbonyldiimidazole (CDI), or conversion of III into its acid chloride and subsequent reaction of the acid chloride of III with IV:

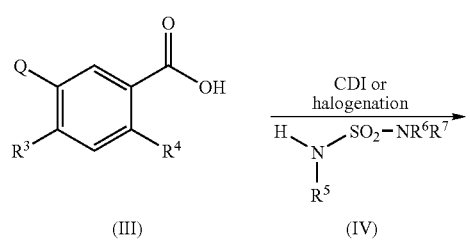

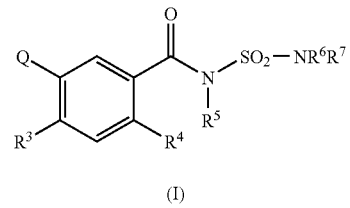

In general, the reaction with IV is preceded by activation of the carboxylic acid III. For activation, it is possible, for example, to convert III into its acid chloride by treatment of the acid III with $SOCl_2$, $POCl_3$, $PCl_5$, $COCl_2$ or $(COCl)_2$. Alternatively, it is possible to prepare the imidazole by reaction of III with N,N-carbonyldiimidazole. These processes are generally known, for example from Houben Weyl, Methoden der Organischen Chemie [Methods of Organic Chemistry], Vol. E5 (1985), Part 1, p. 587 ff. and Vol. E5 (1985), part II, p. 934 ff.

As an alternative to the activation of III via its imidazolides or acid chlorides, it is also possible to use other customary methods of activating carboxylic acids for activating III.

In a typical embodiment, for example, N,N'-carbonyldiimidazole (CDI) is added to a solution of the carboxylic acid III in an inert solvent such as tetrahydrofuran. The resulting mixture is heated, preferably at reflux temperature, until complete conversion has been achieved, and is then cooled. The unsubstituted or substituted sulfonamide IV is added to this mixture, followed, if appropriate, by a nitrogen base, for example a tertiary amine or an amidine base such as diazabicycloundecane (DBU), and the mixture is stirred until the reaction has gone to completion. Conventional work-up and isolation in a customary manner gives the target compound I.

The benzoic acid derivatives III—and their corresponding esters, which can be hydrolyzed in a customary manner to give the free acids III—are known from the prior art or can be prepared in an analogous manner.

Processes for hydrolyzing the esters of III to the corresponding acids are likewise known from the prior art or can be carried out by standard methods for hydrolyzing esters (see also: Kocienski, "Protecting Groups", Thieme Verlag 1994; Greene, Wuts, Protecting groups in organic synthesis, Wiley 1999; Houben-Weyl, Methoden der organischen Chemie [Methods of organic chemistry], Vol. E5, Part I (1985), p. 223 ff.).

The acids III, such as 2-chloro-5-[3,6-dihydro-3-methyl-2,6-dioxo-4-(trifluoromethyl)-$^1$(2H)-pyrimidinyl]-4-fluorobenzoic acid (CAS No. 120890-57-5), and their esters are described, for example, in EP-A 195346, WO 89/02891, prepared in the manner described therein.

B) Reaction of an aniline compound of the formula V with an oxazinone compound VI, giving a 3-phenyluracil of the formula VII which is then alkylated with an alkyl halide:

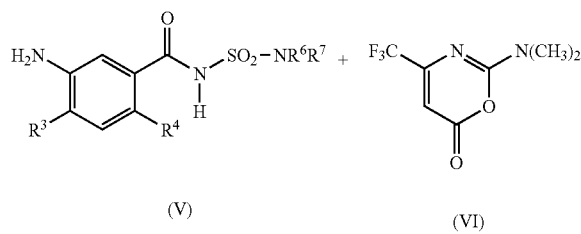

(V)       (VI)

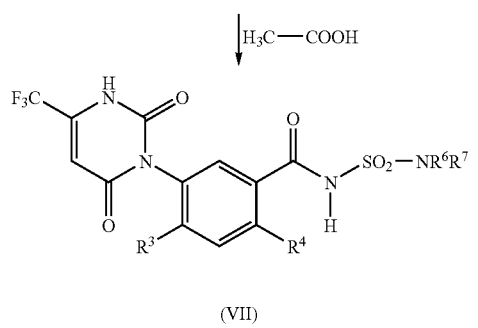

(VII)

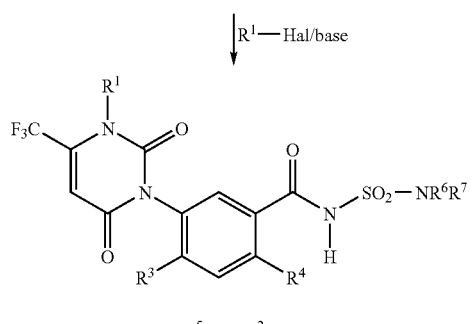

I ($R^5$ = H; $R^2$ = $CF_3$)

The oxazinone compounds VI are known, for example, from WO 99/14216. Here, $R^1$ is preferably methyl.

The reaction of the aniline compound V with the oxazinone VI is usually carried out in a carboxylic acid, for example acetic acid, at temperatures in the range from 0 to 100° C., for example at room temperature, where the components are usually employed in equimolar amounts, or one of the components is employed in excess.

The alkylation of the aniline compound VII at the free uracil nitrogen is achieved in a manner known per se for uracils by reacting VII with an alkylating agent, preferably a methylating agent, for example a methyl halide, preferably methyl iodide, or dimethyl sulfate. The reaction is preferably carried out in the presence of a base, for example an alkali metal hydroxide or alkaline earth metal hydroxide, an alkali metal bicarbonate or, in particular, in the presence of an alkali metal carbonate. The alkylating agent is preferably employed in excess, based on VII. Suitable solvents are, in principle, all inert organic solvents, for example $C_1$-$C_4$-alcohols, haloalkyl compounds such as dichloromethane, ethers such as tetrahydrofuran or dioxane and, preferably, polar aprotic solvents such as dimethylformamide or dimethyl sulfoxide.

The aniline compounds of the formula V can be prepared by customary methods, for example by converting the benzoic acid compound VIII analogously to the procedure described under A into the corresponding N-sulfonylcarboxamide IX, which is initially nitrated and then reduced to give the aniline V:

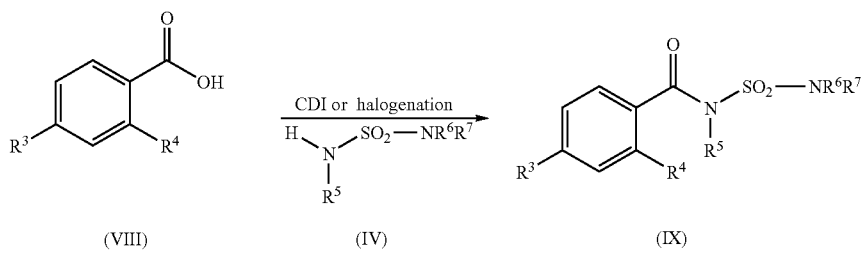

(VIII)      (IV)      (IX)

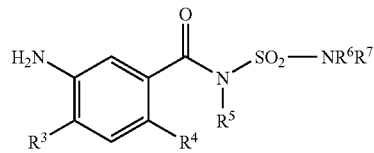

(V)

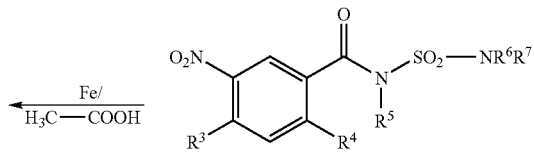

(X)

Suitable nitrating agents are, for example, nitric acid in various concentrations, including concentrated and fuming nitric acid, and also mixtures of nitric acid and sulfuric acid, acyl nitrates and alkyl nitrates.

The nitration can be carried out in the absence of a solvent in an excess of the nitrating agent, or in an inert solvent or diluent, for example in water, in a mineral acid, in organic acids or in anhydrides thereof, such as acetic acid and acetic anhydride, in halogenated hydrocarbons such as methylene chloride, or in mixtures of the abovementioned solvents.

The N-sulfonylbenzamide IX and the nitrating agent can be employed, for example, in equimolar amounts. In terms of the yield of IX, it may be advantageous to employ the nitrating agent in an up to 10-fold molar excess, based on VIII. If the reaction is carried out in the absence of a solvent using the nitrating agent as diluent, the nitrating agent is frequently employed in an even greater excess.

The nitration is usually carried out at temperatures in the range from $(-100)°$ C. to 200° C., preferably in the range from $(-30)$ to 50° C.

The resulting nitro compound X is then reduced by customary methods to give the aniline compound V.

The reduction of X to v can be carried out in a customary manner. Usually, the reduction of X is carried out using a transition metal such as iron, zinc or tin under acidic reaction conditions, or by treating X with a complex hydride such as lithium aluminum hydride or sodium borohydride.

The reduction of X can be carried out in the absence of a solvent or in a solvent or diluent. Examples of suitable solvents are water, alcohols such as methanol, ethanol and isopropanol, and also ethers, for example diethyl ether, methyl tert-butyl ether, dioxane, tetrahydrofuran and ethylene glycol dimethyl ether, where the solvent is chosen in a manner known per se according to the reducing agent used.

If a metal serves as reducing agent, the reduction is preferably carried out in an inorganic acid, in particular in dilute or concentrated hydrochloric acid, or in a liquid organic acid, such as acetic acid or propionic acid. However, it is possible to mix the acid with one of the abovementioned solvents or diluents. The reduction of X with complex hydrides is usually carried out in an organic solvent, preferably in an ether or an alcohol.

Nitro compound X and the reducing agent are frequently employed in approximately equimolar amounts; with respect to optimizing the reaction, it may also be advantageous to employ a relatively large excess of reducing agent, for example an up to 10-fold excess, based on the stoichiometric amount.

The amount of acid is of minor importance. To achieve complete conversion of the starting material, it is recommended to employ at least equimolar amounts of acid. Frequently, the acid is also employed in excess, based on the nitro compound X.

The reduction is usually carried out at temperatures in the range from $(-30)$ to 200° C., preferably in the range from 0 to 80° C.

For work-up, the reaction mixture is usually poured into water, and the aniline compound V is isolated by filtration or extraction with a water-immiscible solvent, for example ethyl acetate, diethyl ether or methylene chloride. If desired, the aniline compound V can be purified in a customary manner, for example by crystallization.

The hydrogenation of the nitro group in X can also be effected by catalytic hydrogenation. Examples of suitable catalysts are Raney-nickel, palladium on activated carbon, palladium oxide, platinum and platinum oxide. The amount of catalyst is usually in the range from 0.05 to 50 mol%, based on the nitro compound X to be reduced.

The hydrogen partial pressure required for the hydrogenation is usually in the range from atmospheric pressure to 50 bar.

The catalytic hydrogenation is frequently carried out in an inert solvent, for example in acetic acid, acetic acid/water mixtures, ethyl acetate or toluene. Following the removal of the catalyst, the reaction mixture is worked up in a customary manner, giving the aniline compound V.

Further suitable methods can be found in the literature (see, for example, Houben-Weyl, Methoden der Organischen Chemie, stickstoffverbindungen [Nitrogen compounds] I, Part 1 (1971), Vol. X/1, p. 463 ff.).

Further methods which can be used in a similar manner for preparing the phenyluracils I are described in Böger, Wakabayashi: Peroxidizing herbicides, Springer Verlag 1999.

Analogously to the synthesis route described here under B, it is also possible to prepare the carboxylic acid III starting from the carboxylic acid VIII.

C) Replacement of a halogen radical by a uracil radical Q:

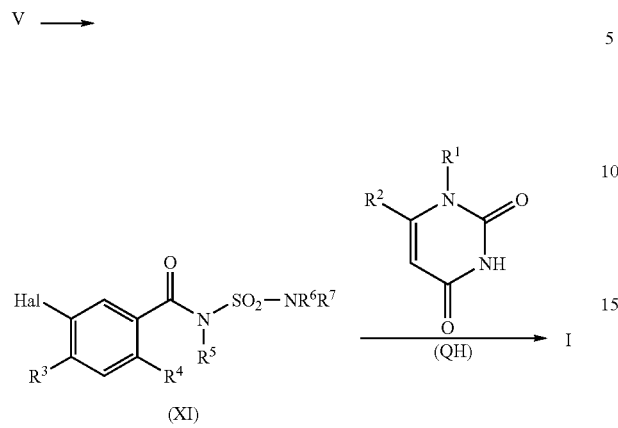

(XI)

Hal=Halogen, preferably bromine or iodine.

Here, the aniline V is initially converted into the corresponding diazonium salt which is then, in a Sandmeyer reaction in a manner known per se, converted into the halogen compound XI, for example by treatment with copper(I) halide or copper(II) halide or, in the case of the iodide XI (Hal=I), also by treatment of the diazonium salt of V with iodine/potassium-iodide. These methods are generally known to the person skilled in the art, for example from Houben-Weyl, Methoden der Org. Chemie, Vol. 5/4, 4th edition 1960, p. 438 ff.

The reaction of XI with a uracil compound QH, preferably in the presence of a copper(I) compound as catalyst, then affords the corresponding 3-phenyluracil I.

By this route, it is also possible to prepare phenyluracils I where Hal=iodine similarly to the methods described by T. Maruyama, K. Fujiwara and M. Fukuhara in J. Chem. Soc., Perkin Trans. 1995 (7), pp. 733-734, using Cu(I) compounds.

D) Reaction of the benzoic ester XII, for example the methyl ester, with an electrophilic aminating agent, giving 3-(1-aminouracil-3-yl)benzoic ester XIII, hydrolysis of XIII to give 3-(1-aminouracil-3-yl)benzoic acid XIV (where $R^1=NH_2$) and conversion of XIV by the method described under A into the compound I where $R^1=NH_2$:

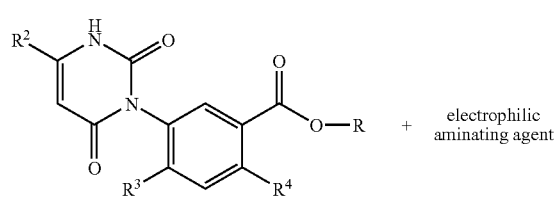

(XII; R = $C_1$–$C_4$-alkyl)

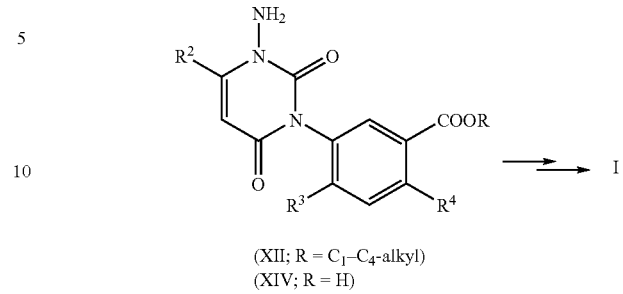

(XII; R = $C_1$–$C_4$-alkyl)
(XIV; R = H)

Examples of electrophilic aminating agents are 2,4-dinitro-phenylhydroxylamine and O-mesitylenesulfonylhydroxylamine. Suitable reaction conditions for the electrophilic amination are given in DE-A 19 652 431, the disclosure of which on the electrophilic amination is expressly incorporated herein by way of reference.

The esters XII can be prepared from the corresponding 3-aminobenzoic acids or 3-aminobenzoic esters using the methods described under B. The hydrolysis of XIII to acid XIV is carried out by customary methods, for example in the presence of catalytic amounts of a mineral acid such as hydrochloric acid or sulfuric acid, or in the presence of an organic sulfonic acid, preferably in an aqueous or aqueous-alcoholic solvent. Alternatively, the "hydrolysis" can also be carried out under nonaqueous reaction conditions, for example by successive cleavage with a halogen transfer reagent such as boron tribromide or trimethylsilyl iodide and subsequent aqueous work-up.

In the preparation, the 3-phenyluracils I to be used according to the invention can be obtained as isomer mixtures which can be separated into the pure isomers using conventional methods, for example crystallization, chromatography and the like.

For further details about the preparation of the ³-phenyluracils I, reference is made to PCT EP/01/04850, in particular to the preparation examples.

USE EXAMPLES

The effect of the herbicidal mixtures according to the invention of components A and B and, if appropriate, C on the growth of undesirable plants compared to the herbicidally active compounds alone was demonstrated by the following greenhouse experiments (Examples 1 to 11):

For the post-emergence treatment, the test plants were first grown to a height of 3 to 20 cm, depending on the plant habit, and only then treated. Here, the herbicidal compositions were suspended or emulsified in water as distribution medium and sprayed using finely distributing nozzles The respective components A and B and/or C were formulated as 10% by weight strength emulsion concentrate and introduced to the spray liquor with the amount of solvent system used for applying the active compound. In the examples, the solvent used was water.

The test period extended over 21 days. During this time, the plants were tended, and their response to the treatments with active compound was evaluated.

The evaluation for the damage caused by the chemical compositions was carried out using a scale from 0 to 100%, compared to the untreated control plants. Here, 0 means no damage and 100 means complete destruction of the plants.

In the examples below, the value E which is to be expected if the activity of the individual compounds is just additive was calculated using the method of S. R. Colby (1967) "Calculating synergistic and antagonistic responses of herbicide combinations", Weeds 15, p. 22 ff.

$$E = X + Y - (X \cdot Y / 100)$$

where

X=effect in percent using active compound A at an application rate a;
Y=effect in percent using active compound B at an application rate b;
E=expected effect (in %) of A+B at application rates a+b.

If the observed effect is higher than the value E calculated according to Colby, a synergistic effect is present.

The following active compounds were tested:
phenyluracil I.1 from Table 1 (Example 54 of PCT/EP01/04850);
phenyluracil I.7 from Table 1 (Example 101 of PCT/EP01/04850);
phenyluracil I.8 from Table 1 (Example 76 of PCT/EP01/04850);
phenyluracil I.14 from Table 1 (Example 127 of PCT/EP01/04850);
tralkoxydim (group b1): herbicide b1.1;
profoxydim (group b1): herbicide b1.2;
fenoxaprop-P-ethyl (group b1): herbicide b1.3;
imazamox (group b2): herbicide b2.1;
imazethapyr (group b2): herbicide b2.2;
nicosulfuron (group b2): herbicide b2.3;
atrazine (group b3): herbicide b3.1;
diuron (group b3): herbicide b3.2;
isoproturon (group b3): herbicide b3.3;
paraquat (group b3): herbicide b3.4;
cinidon-ethyl (group b4): herbicide b4.1;
picolinafen (group b5): herbicide b5.1;
sulcotrione (group b5): herbicide b5.2;
glyphosate isopropylammonium salt (group b6): herbicide b6.1;
glufosinate ammonium salt (group b7): herbicide b7.1;
pendimethalin (group b9): herbicide b9.1;
dimethenamid-P (group b10): herbicide b10.1;
acetochlor (group b10): herbicide b10.2;
S-metolachlor (group b10): herbicide b10.3;
isoxaben (group b11): herbicide b11.1;
dichlorprop-P dimethylammonium salt (group b13): herbicide b13.1;
dicamba (group b13):-herbicide b13.2;
2,4-D dimethylammonium salt (group b13): herbicide b13.3;
diflufenzopyr sodium salt (group b14): herbicide b14.1;
oxaziclomefone (group b15): herbicide b15.1;
mefenpyr-diethyl: Safener c.1;
benoxacor: Safener c.2.

The following test plants were used for the greenhouse experiments:

| Bayer code | Botanical name |
|---|---|
| ABUTH | *Abutilon theophrasti* |
| ALOMY | *Alopecurus myosuroides* |
| AMARE | *Amaranthus retroflexus* |
| AVEFA | *Avena fatua* |
| BIDPI | *Bidens pilosa* |
| BRAPL | *Brachiaria plantaginea* |
| COMBE | *Commelina benghalensis* |
| ECHCG | *Echinochloa crus-galli* |
| GALAP | *Galium aparine* |
| POLPE | *Polygonum persicaria* |
| POAPR | *Poa pratensis* |
| SETFA | *Setaria faberii* |
| TRFPR | *Trifolium pratense* |
| TRZAW | *Triticum aestivum* (Winter wheat) |

The results of these tests are given in the tables of Examples 1 to 26 below, and they demonstrate the synergistic action of mixtures comprising at least one phenyluracil I and at least one herbicide B.

EXAMPLE 1

Herbicidal action of the mixture 8.124, applied by the post-emergence method, against ALOMY

| Application rate in g/ha | | Herbicidal action against ALOMY | |
|---|---|---|---|
| I.8 | b2.1 | found | calculated |
| 0.49 | — | 5 | — |
| — | 7.81 | 40 | — |
| 0.49 | 7.81 | 80 | 43 |
| 0.98 | — | 10 | — |
| — | 15.63 | 70 | — |
| 0.98 | 15.63 | 85 | 73 |

EXAMPLE 2

Herbicidal action of the mixture 8.128, applied by the post-emergence method, against BIDPI

| Application rate in g/ha | | Herbicidal action against BIDPI | |
|---|---|---|---|
| I.8 | b2.2 | found | calculated |
| 0.49 | — | 10 | — |
| — | 7.81 | 20 | — |
| 0.49 | 7.81 | 50 | 28 |
| 0.98 | — | 20 | — |
| — | 15.63 | 20 | — |
| 0.98 | 15.63 | 70 | 36 |

EXAMPLE 3

Herbicidal action of the mixture 7.140, applied by the post-emergence method, against AVEFA and against POLPE

| Application rate in g/ha | | Herbicidal action against AVEFA | | Herbicidal action against POLPE | |
|---|---|---|---|---|---|
| I.7 | b3.1 | found | calculated | found | calculated |
| 1.95 | — | 10 | — | 0 | — |
| — | 62.5 | 0 | — | 50 | — |
| 1.95 | 62.5 | 40 | 10 | 85 | 50 |
| 3.91 | — | 15 | — | 25 | — |
| — | 125 | 0 | — | 60 | — |
| 3.91 | 125 | 50 | 15 | 98 | 70 |

EXAMPLE 4

Herbicidal action of the mixture 7.151, applied by the post-emergence method, against BRAPL and against ECHCG

| Application rate in g/ha | | Herbicidal action against BRAPL | | Herbicidal action against ECHCG | |
|---|---|---|---|---|---|
| I.7 | b3.2 | found | calculated | found | calculated |
| 1.95 | — | 40 | — | 0 | — |
| — | 62.5 | 25 | — | 15 | — |
| 1.95 | 62.5 | 70 | 55 | 25 | 15 |
| 3.91 | — | 60 | — | 30 | — |
| — | 125 | 60 | — | 20 | — |
| 3.91 | 125 | 98 | 84 | 70 | 44 |

EXAMPLE 5

Herbicidal action of the mixture 7.152, applied by the post-emergence method, against ABUTH

| Application rate in g/ha | | Herbicidal action against ABUTH | |
|---|---|---|---|
| I.7 | b3.3 | found | calculated (according to Colby) |
| 0.98 | — | 0 | — |
| — | 31.25 | 0 | — |
| 0.98 | 31.25 | 60 | 0 |
| 1.95 | — | 30 | — |
| — | 62.5 | 40 | — |
| 1.95 | 62.5 | 98 | 58 |

EXAMPLE 6

Herbicidal action of the mixture 7.162, applied by the post-emergence method, against ABUTH

| Application rate in g/ha | | Herbicidal action against ABUTH | |
|---|---|---|---|
| I.7 | b3.4 | found | calculated (according to Colby) |
| 0.98 | — | 0 | — |
| — | 31.25 | 0 | — |
| 0.98 | 31.25 | 50 | 0 |
| 1.95 | — | 30 | — |
| — | 62.5 | 40 | — |
| 1.95 | 62.5 | 80 | 58 |

EXAMPLE 7

Herbicidal action of the mixture 8.188, applied by the post-emergence method, against BRAPL and against POLPE

| Application rate in g/ha | | Herbicidal action against BRAPL | | Herbicidal action against POLPE | |
|---|---|---|---|---|---|
| I.8 | b5.1 | found | calculated | found | calculated |
| 0.98 | — | 30 | — | 10 | — |
| — | 7.81 | 20 | — | 30 | — |
| 0.98 | 7.81 | 65 | 44 | 40 | 36 |
| 1.95 | — | 40 | — | 20 | — |
| — | 15.63 | 20 | — | 40 | — |
| 1.95 | 15.63 | 75 | 52 | 60 | 52 |

EXAMPLE 8

Herbicidal action of the mixture 8.194, applied by the post-emergence method, against ECHCG

| Application rate in g/ha | | Herbicidal action against ECHCG | |
|---|---|---|---|
| I.8 | b5.2 | found | calculated |
| 1.95 | — | 20 | — |
| — | 31.25 | 60 | — |
| 1.95 | 31.25 | 100 | 68 |
| 3.91 | — | 40 | — |
| — | 62.5 | 75 | — |
| 3.91 | 62.5 | 100 | 85 |

EXAMPLE 9

Herbicidal action of the mixture 7.206, applied by the post-emergence method, against AVEFA

| Application rate in g/ha | | Herbicidal action against AVEFA | |
|---|---|---|---|
| I.7 | b6.1 | found | calculated |
| 1.95 | — | 10 | — |
| — | 125 | 0 | — |
| 1.95 | 125 | 25 | 10 |
| 3.91 | — | 15 | — |
| — | 250 | 0 | — |
| 3.91 | 250 | 60 | 15 |

EXAMPLE 10

Herbicidal action of the mixture 7.207, applied by the post-emergence method, against AVEFA and against POLPE

| Application rate in g/ha | | Herbicidal action against AVEFA | | Herbicidal action against POLPE | |
|---|---|---|---|---|---|
| I.7 | b7.1 | found | calculated | found | calculated |
| 1.95 | — | 10 | — | 0 | — |
| — | 250 | 0 | — | 0 | — |
| 1.95 | 250 | 25 | 10 | 40 | 0 |
| 3.91 | — | 15 | — | 25 | — |
| — | 500 | 20 | — | 30 | — |
| 3.91 | 500 | 70 | 32 | 70 | 47.5 |

EXAMPLE 11

Herbicidal action of the mixture 7.283, applied by the post-emergence method, against COMBE and against POLPE

| Application rate in g/ha | | Herbicidal action against COMBE | | Herbicidal action against POLPE | |
|---|---|---|---|---|---|
| I.7 | b13.1 | found | calculated | found | calculated |
| 1.95 | — | 0 | — | 0 | — |
| — | 500 | 40 | — | 30 | — |
| 1.95 | 500 | 85 | 40 | 70 | 30 |
| 3.91 | — | 0 | — | 25 | — |
| — | 1000 | 75 | — | 30 | — |
| 3.91 | 1000 | 85 | 75 | 85 | 47.5 |

EXAMPLE 12

Herbicidal action of the mixture 1.64, applied by the post-emergence method, against GALAP

| Application rate in g/ha | | Herbicidal action against GALAP | |
|---|---|---|---|
| I.1 | b1.1 | found | calculated |
| 1.95 | — | 20 | — |
| — | 62.5 | 0 | — |
| 1.95 | 62.5 | 30 | 20 |
| 3.91 | — | 20 | — |
| — | 125 | 0 | — |
| 3.91 | 125 | 40 | 20 |

EXAMPLE 13

Herbicidal action of the mixture 1.61, applied by the post-emergence method, against ABUTH

| Application rate in g/ha | | Herbicidal action against ABUTH | |
|---|---|---|---|
| I.1 | b1.2 | found | calculated |
| 1.95 | — | 20 | — |
| — | 31.25 | 30 | — |
| 1.95 | 31.25 | 100 | 44 |
| 3.91 | — | 30 | — |
| — | 62.5 | 40 | — |
| 3.91 | 62.5 | 100 | 58 |

EXAMPLE 14

Herbicidal action of the mixture 1.25, applied by the post-emergence method, against GALAP

| Application rate in g/ha | | Herbicidal action against GALAP | |
|---|---|---|---|
| I.1 | b1.3 + c.1 | found | calculated |
| 1.95 | — | 50 | — |
| — | 62.5 + 67.5 | 0 | — |
| 1.95 | 62.5 + 67.5 | 60 | 50 |
| 3.91 | — | 60 | — |
| — | 125 + 135.9 | 0 | — |
| 3.91 | 125 + 135.9 | 80 | 60 |

EXAMPLE 15

Herbicidal action of the mixture 14.107, applied by the post-emergence method, against ALOMY and against BRAPL

| Application rate in g/ha | | Herbicidal action against ALOMY | | Herbicidal action against BRAPL | |
|---|---|---|---|---|---|
| I.14 | b2.3 | found | calculated | found | calculated |
| 0.49 | — | 0 | — | 0 | — |
| — | 0.98 | 50 | — | 70 | — |
| 0.49 | 0.98 | 80 | 50 | 80 | 70 |
| 0.98 | — | 0 | — | 0 | — |
| — | 1.95 | 60 | — | 70 | — |
| 0.98 | 1.95 | 80 | 60 | 80 | 70 |

EXAMPLE 16

Herbicidal action of the mixture 1.170, applied by the post-emergence method, against POLPE

| Application rate in g/ha | | Herbicidal action against POLPE | |
|---|---|---|---|
| I.1 | b4.1 | found | calculated |
| 0.49 | — | 10 | — |
| — | 0.98 | 40 | — |
| 0.49 | 0.98 | 60 | 46 |
| 0.98 | — | 25 | — |
| — | 1.95 | 50 | — |
| 0.98 | 1.95 | 85 | 62.5 |

EXAMPLE 17

Herbicidal action of the mixture 1.213, applied by the post-emergence method, against AVEFA

| Application rate in g/ha | | Herbicidal action against AVEFA | |
|---|---|---|---|
| I.1 | b9.1 | found | calculated |
| 0.98 | — | 5 | — |
| — | 125 | 10 | — |
| 0.98 | 125 | 30 | 14.5 |
| 1.95 | — | 10 | — |
| — | 250 | 20 | — |
| 1.95 | 250 | 40 | 28 |

EXAMPLE 18

Herbicidal action of the mixture 1.238, applied by the post-emergence method, against AVEFA and against BIDPI

| Application rate in g/ha | | Herbicidal action against AVEFA | | Herbicidal action against BIDPI | |
|---|---|---|---|---|---|
| I.1 | b10.1 | found | calculated | found | calculated |
| 1.95 | — | 10 | — | 40 | — |
| — | 125 | 30 | — | 25 | — |
| 1.95 | 125 | 60 | 37 | 85 | 55 |
| 3.91 | — | 10 | — | 50 | — |
| — | 250 | 30 | — | 25 | — |
| 3.91 | 250 | 80 | 37 | 100 | 62.5 |

EXAMPLE 19

Herbicidal action of the mixture 14.216, applied by the post-emergence method, against BIDPI

| Application rate in g/ha | | Herbicidal action against BIDPI | |
|---|---|---|---|
| I.14 | b10.2 | found | calculated |
| 1.95 | — | 40 | — |
| — | 250 | 30 | — |
| 1.95 | 250 | 98 | 58 |
| 3.91 | — | 85 | — |
| — | 500 | 70 | — |
| 3.91 | 500 | 98 | 95.5 |

EXAMPLE 20

Herbicidal action of the mixture 14.288, applied by the post-emergence method, against ECHCG

| Application rate in g/ha | | Herbicidal action against ECHCG | |
|---|---|---|---|
| I.14 | b13.2 | found | calculated |
| 1.95 | — | 40 | — |
| — | 125 | 0 | — |
| 1.95 | 125 | 60 | 40 |
| 3.91 | — | 70 | — |
| — | 250 | 30 | — |
| 3.91 | 250 | 95 | 79 |

EXAMPLE 21

Herbicidal action of the mixture 1.296, applied by the post-emergence method, against AMARE and against BIDPI

| Application rate in g/ha | | Herbicidal action against AMARE | | Herbicidal action against BIDPI | |
|---|---|---|---|---|---|
| I.1 | b14.1 | found | calculated | found | calculated |
| 0.49 | — | 60 | — | 20 | — |
| — | 7.81 | 0 | — | 20 | — |
| 0.49 | 7.81 | 80 | 50 | 50 | 36 |
| 0.98 | — | 60 | — | 30 | — |
| — | 15.63 | 0 | — | 30 | — |
| 0.98 | 15.63 | 80 | 60 | 60 | 51 |

EXAMPLE 22

Herbicidal action of the mixture 14.253, applied by the post-emergence method, against SETFA and against GALAP

| Application rate in g/ha | | Herbicidal action against SETFA | | Herbicidal action against GALAP | |
|---|---|---|---|---|---|
| I.14 | b10.3 | found | calculated | found | calculated |
| 0.49 | — | 20 | — | 0 | — |
| — | 62.5 | 30 | — | 0 | — |
| 0.49 | 62.5 | 70 | 44 | 30 | 0 |
| 0.98 | — | 25 | — | 25 | — |
| — | 125 | 60 | — | 25 | — |
| 0.98 | 125 | 75 | 70 | 50 | 43.75 |

EXAMPLE 23

Herbicidal action of the mixture 14.258, applied by the post-emergence method, against SETFA and against GALAP

| Application rate in g/ha | | Herbicidal action against SETFA | | Herbicidal action against GALAP | |
|---|---|---|---|---|---|
| I.14 | b10.3 + c.2 | found | calculated | found | calculated |
| 0.49 | — | 20 | — | 0 | — |
| — | 62.5 + 3.13 | 0 | — | 0 | — |
| 0.49 | 62.5 + 3.13 | 60 | 20 | 30 | 0 |
| 0.98 | — | 25 | — | 25 | — |
| — | 125 + 6.25 | 30 | — | 0 | — |
| 0.98 | 125 + 6.25 | 75 | 47.5 | 50 | 25 |

EXAMPLE 24

Herbicidal action of the mixture 14.280, applied by the post-emergence method, against BRAPL and against ABUTH

| Application rate in g/ha | | Herbicidal action against BRAPL | | Herbicidal action against ABUTH | |
|---|---|---|---|---|---|
| I.14 | b13.3 | found | calculated | found | calculated |
| 0.49 | — | 10 | — | 0 | — |
| — | 62.5 | 20 | — | 25 | — |
| 0.49 | 62.5 | 40 | 28 | 95 | 25 |
| 0.98 | — | 15 | — | 20 | — |
| — | 125 | 50 | — | 65 | — |
| 0.98 | 125 | 60 | 7.5 | 95 | 72 |

EXAMPLE 25

Herbicidal action of the mixture 14.279, applied by the post-emergence method, against SETFA and against GALAP

| Application rate in g/ha | | Herbicidal action against SETFA | | Herbicidal action against GALAP | |
|---|---|---|---|---|---|
| I.14 | b11.1 | found | calculated | found | calculated |
| 0.49 | — | 20 | — | 0 | — |
| — | 62.5 | 0 | — | 0 | — |
| 0.49 | 62.5 | 40 | 20 | 20 | 0 |
| 0.98 | — | 25 | — | 25 | — |
| — | 125 | 10 | — | 0 | — |
| 0.98 | 125 | 50 | 32.5 | 50 | 25 |

EXAMPLE 26

Herbicidal action of the mixture 14.300, applied by the post-emergence method, against COMBE

| Application rate in g/ha | | Herbicidal action against COMBE | |
|---|---|---|---|
| I.14 | b.15.1 | found | calculated |
| 1.95 | — | 0 | — |
| — | 125 | 0 | — |
| 1.95 | 125 | 40 | 0 |
| 3.91 | — | 40 | — |
| — | 250 | 0 | — |
| 3.91 | 250 | 60 | 40 |

Safener Action

In the examples below, the mixtures were applied by the pre-emergence method. To this end, the test plants were initially sown and covered with a thin layer of soil. Afterward (i.e. prior to the germination of the test plants), the mixtures according to the invention were sprayed onto the soil as an aqueous spray liquor at the stated application rate. As in the post-emergence method described above, the test period was 21 days. The damage was then evaluated as described above using a scale from 0 to 100% damage in comparison to untreated control plants (0% damage).

A safener action is present if the damage to the crop plant caused by using a mixture according to the invention which contains a safener C) is less than the damage caused when active compound A or active compounds A and B are used without safener.

EXAMPLE 27

Herbicidal action of the mixture 7.314 against POAPR and against TRFPR and safener action in the case of TRZAW

| Application rate in g/ha | | Damage to crop plant | Herbicidal action against | Herbicidal action against |
|---|---|---|---|---|
| I.7 | c.1 | TRZAW | POAPR | TRFPR |
| 200 | — | 10 | 98 | 100 |
| — | 200 | 0 | 0 | 5 |
| 200 | 200 | 5 | 95 | 100 |
| 400 | — | 35 | 98 | 100 |
| — | 400 | 0 | 0 | 5 |
| 400 | 400 | 15 | 98 | 100 |

EXAMPLE 28

Herbicidal action of the mixture 8.314 against POAPR and against TRFPR and safener action in the case of TRZAW

| Application rate in g/ha | | Damage to crop plant | Herbicidal action against | Herbicidal action against |
|---|---|---|---|---|
| I.8 | c.1 | TRZAW | POAPR | TRFPR |
| 200 | — | 30 | 98 | 100 |
| — | 200 | 0 | 0 | 5 |
| 200 | 200 | 10 | 98 | 100 |
| 400 | — | 65 | 100 | 100 |
| — | 400 | 0 | 0 | 5 |
| 400 | 400 | 20 | 100 | 100 |

We claim:

1. A herbicidally active composition, comprising:
A) at least one phenyluracil compound of the formula I

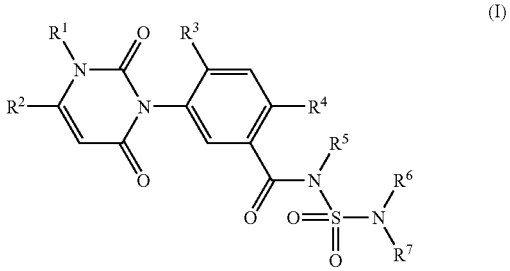

(I)

in which the variables $R^1$-$R^7$ are as defined below:
$R^1$ is methyl or $NH_2$;
$R^2$ is $C_1$-$C_2$-haloalkyl;
$R^3$ is hydrogen or halogen;
$R^4$ is halogen or cyano;
$R^5$ is hydrogen, cyano, $C_1$-$C_6$-alkyl, $C_1$-$C_6$-alkoxy, $C_1$-$C_4$-alkoxy-$C_1$-$C_4$-alkyl, $C_3$-$C_7$-cycloalkyl, $C_3$-$C_6$-alkenyl, $C_3$-$C_6$-alkynyl or benzyl which is unsubstituted or substituted by halogen or alkyl;
$R^6$, $R^7$ independently of one another are hydrogen, $C_1$-$C_6$-alkyl, $C_1$-$C_6$-alkoxy, $C_3$-$C_6$-alkenyl, $C_3$-$C_6$-alkynyl, $C_3$-$C_7$-cycloalkyl, $C_3$-$C_7$-cycloalkenyl, phenyl or benzyl, where each of the 8 abovementioned substituents is unsubstituted or may be substituted by 1 to 6 halogen atoms and/or by one, two or three groups selected from: OH, $NH_2$, CN, $CONH_2$, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfonyl, $C_1$-$C_4$-haloalkylsulfonyl, $C_1$-$C_4$-alkylamino, di($C_1$-$C_4$-alkyl)amino, formyl, $C_1$-$C_4$-alkylcarbonyl, $C_1$-$C_4$-alkoxycarbonyl, $C_1$-$C_4$-alkylaminocarbonyl, di($C_1$-$C_4$-alkyl)aminocarbonyl, $C_3$-$C_7$-cycloalkyl, phenyl and benzyl; or
$R^6$, $R^7$ together with the nitrogen atom form a 3-, 4-, 5-, 6- or 7-membered saturated or unsaturated nitrogen heterocycle which may be substituted by 1 to 6 methyl groups and which may contain 1 or 2 further heteroatoms selected from the group consisting of nitrogen, oxygen and sulfur as ring members,
and/or at least one of its agriculturally acceptable salts;
and at least one further active compound selected from
B) herbicides of classes b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors;
b5) bleacher herbicides;
b6) enolpyruvyl shikimate 3-phosphate synthase inhibitors (EPSP inhibitors);
b7) glutamine synthetase inhibitors;
b9) mitose inhibitors;
b10) inhibitors of the synthesis of very long chain fatty acids (VLCFA inhibitors);
b11) cellulose biosynthesis inhibitors;
b13) auxin herbicides;
b14) auxin transport inhibitors;
b15) other herbicides selected from the group consisting of benzoylprop, flamprop, flamprop-M, bromobutide, chlorflurenol, cinmethylin, methyldymuron, etobenzanid, fosamine, metam, pyributicarb, oxaziclomefone, dazomet, triaziflam and methyl bromide; and
C) safeners selected from: benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloroacetyl)-1,3-oxazolidine and oxabetrinil,
agriculturally acceptable salts of the active compounds B and C and agriculturally acceptable esters, amides and thioesters of such active compounds B and C which have a carboxyl group,
wherein the phenyluracil compound(s) of formula (I) and the further active compound(s) are present in synergistically effective amounts.

2. A composition as claimed in claim 1, wherein the variables $R^1$ to $R^7$ in formula I independently of one another have the following meanings:
$R^1$ is methyl or $NH_2$;
$R^2$ is trifluoromethyl;
$R^3$ is hydrogen, fluorine or chlorine;
$R^4$ is halogen or cyano;
$R^5$ is hydrogen;
$R^6$, $R^7$ independently of one another are hydrogen, $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkenyl, phenyl or benzyl or
$R^6$, $R^7$ together with the nitrogen atom form a pyrrolidine, piperidine, morpholine, N-methylpiperazine or perhydroazepine ring.

3. A composition as claimed in claim 2, wherein the variables $R^1$ to $R^7$ in formula I have the following meanings:
$R^1$ is methyl;
$R^2$ is trifluoromethyl;
$R^3$ is fluorine;
$R^4$ is chlorine;
$R^5$ is hydrogen;

$R^6$, $R^7$ independently of one another are $C_1$-$C_6$-alkyl.

4. A composition as claimed in claim 2, wherein the variables $R^1$ to $R^7$ in formula I have the following meanings:
$R^1$ is $NH_2$;
$R^2$ is trifluoromethyl;
$R^3$ is fluorine;
$R^4$ is chlorine;
$R^5$ is hydrogen;
$R^6$, $R^7$ independently of one another are $C_1$-$C_6$-alkyl.

5. A composition as claimed in claim 1, comprising at least one herbicide B selected from the compounds listed below:

b1) from the group of the lipid biosynthesis inhibitors: chlorazifop, clodinafop, clofop, cyhalofop, diclofop, fenoxa-prop, fenoxaprop-p, fenthiaprop, fluazifop, fluazifop-P, haloxyfop, haloxyfop-P, isoxapyrifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate and bensulide;

b2) from the group of the ALS inhibitors: amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac;

b3) from the group of the photosynthesis inhibitors: atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluron, phenobenzuron, siduron, tetrafluron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate, and pyridafol;

b4) from the group of the protoporphyrinogen-IX oxidase inhibitors: acifluorfen, bifenox, chiomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidonethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen and etnipromid;

b5) from the group of the bleacher herbicides: metfiurazon, norflurazon, flufenican, diflufenican, picolinafen, beflubutamid, fluridone, flurochloridone, flurtamone, mesotrione, sulcotrione, isoxachlortole, isoxaflutole, benzofenap, pyrazolynate, pyrazoxyfen, benzobicyclon, amitrole, clomazone, aclonifen, and also 3-heterocyclyl-substituted benzoyl compounds of the formula II

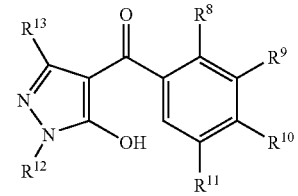

in which the variables $R^8$ to $R^{13}$ are as defined below:

$R^8$, $R^{10}$ are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl or $C_1$-$C_6$-alkylsulfonyl;

$R^9$ is a heterocyclic radical selected from the group consisting of: thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, where the nine radicals mentioned may be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;

$R^{11}$ is hydrogen, halogen or $C_1$-$C_6$-alkyl;
$R^{12}$ is $C_1$-$C_6$-alkyl;
$R^{13}$ is hydrogen or $C_1$-$C_6$-alkyl;

b6) from the group of the EPSP synthase inhibitors: glyphosate;

b7) from the group of the glutamine synthase inhibitors: glufosinate and bilanaphos;

b9) from the group of the mitose inhibitors: benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;

b10) from the group of the VLCFA inhibitors: acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachbor, allidochlor, CDEA, epronaz, diphenamid, napropamide, naproanilide, pethoxamid, flufenacet, mefenacet, fentrazamide, anilofos, piperophos, cafenstrole, indanofan and tridiphane;

b11) from the group of the cellulose biosynthesis inhibitors: dichlobenil, chlorthiamid, isoxaben and flupoxam;

b13) from the group of the auxin herbicides: clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quincborac, quinmerac, cbopyralid, fluroxypyr, picloram, tricbopyr and benazolin;

b14) from the group of the auxin transport inhibitors: naptalam, diflufenzopyr;

b15) benzoylprop, flamprop, flamprop-M, bromobutide, chlorflurenol, cinmethylin, methyldymron, etobenzanid, fosamine, metam, pyributicarb, oxaziclomefone, dazomet, triaziflam and methyl bromide;

agriculturally acceptable salts and agriculturally acceptable esters, amides and thioesters of such herbicides B which have a carboxyl group.

6. A composition as claimed in claim 5, wherein the herbicides B are selected from:

b1) clodinafop, cyhalofop, diclofop, fenoxaprop, fenoxaprop-P, fluazifop, fluazifop-P, haloxyfop, haloxyfop-P, quizalofop, quizalofop-P, alloxydim, butroxydim, clethodim, cloproxydim, cycloxydim, profoxydim, sethoxydim, tepraloxydim, tralkoxydim;

b2) amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, propoxycarbazone, flucarbazone, imazamethabenz, imazamox, imazapic, imazapyr, imazaquin, imazethapyr, cloransulam, diclosulam, florasulam, flumetsulam, metosulam, penoxsulam, bispyribac, pyribenzoxim, pyriftalid, pyrithiobac, pyriminobac;

b3) atrazine, cyanazine, simazine, terbuthylazine, hexazinone, metamitron, metribuzin, amicarbazone, chloridazon, chlorbromuron, chlorotoluron, diuron, isoproturon, linuron, methabenzthiazuron, propanhl, bromoxynil, ioxynil, bentazone, pyridate, difenzoquat, diquat, paraquat;

b4) acifluorfen, fluoroglycofen, halosafen, lactofen, oxyfluorfen, fluazolate, pyraflufen, cinidon-ethyl, flumiclorac, flumioxazin, fluthiacet, oxadiazon, oxadiargyl, azafenidin, carfentrazone, sulfentrazone, pentoxazone, benzfendizone, butafenacil, pyraclonhl, profluazol, flufenpyr, nipyraclofen;

b5) norflurazon, diflufenican, picolinafen, beflubutamid, fluridone, flurochloridone, flurtamone, mesotrione, sulcotrione, isoxachlortole, isoxaflutole, benzofenap, pyrazolynate, pyrazoxyfen, benzobicyclon, clomazone, and also [2-chloro-3-(4,5-dihydro-3-isoxazolyl)-4-(methylsulfonyl)phenyl](5-hydroxy-1-methyl-1H-pyrazol-4-yl)methanone, [3-(4,5-dihydro-3-isoxazolyl)2-methyl-4-(methylsulfonyl)phenyl](5-hydroxy-1-methyl-1H-pyrazol-4-yl)methanone, [2-chloro-3-(3-methyl-5-isoxazolyl)-4-(methylsulfonyl)-phenyl](5-hydroxy-1-methyl-1H-pyrazol-4-yl)methanone, (5-hydroxy-1-methyl-1H-pyrazol-4-yl)[2-methyl-3-(3-methyl-5-isoxazolyl)-4-(methylsulfonyl)phenyl]methanone;

b6) glyphosate;

b7) glufosinate;

b9) benfluralin, butralin, dinitramine, ethalfiuralin, oryzalin, pendimethalin, trifluralin, propyzamide;

b10) acetochlor, alachlor, butachlor, dimethenamid, dimethenamid-P, metazachlor, metolachlor, S-metolachlor, pethoxamid, pretilachlor, propachlor, propisochlor, thenyichlor, flufenacet, mefenacet, fentrazamide, cafenstrole, indanofan;

b11) dichlobenil, chlorthiamid, isoxaben, flupoxam;

b13) 2,4-D, 2,4-DB, dichlorprop, dichlorprop-P, MCPA, MCPB, mecoprop, mecoprop-P, dicamba, quinclorac, quinmerac, clopyralid, fluroxypyr, picloram, triclopyr, benazolin;

b14) diflufenzopyr;

b15) bromobutide, cinmethylin, methyldymron, oxaziclomefone, triaziflam;

agriculturally acceptable salts of the abovementioned active compounds B and agriculturally acceptable esters, amides and thioesters of such active compounds B which have a carboxyl group.

7. A composition as claimed in claim 5, comprising at least one 3-heterocyclyl-substituted benzoyl compound of the formula II, where the variables $R^8$ to $R^{13}$ are as defined below:

$R^8$ is halogen or $C_1$-$C_4$-alkyl;

$R^9$ is a heterocyclic radical selected from the group consisting of: isoxazol-3-yl, isoxazol-5-yl, 4,5-dihydroisoxazol-3-yl, where the three radicals mentioned may be unsubstituted or mono- or disubstituted by halogen, $C_1$-$C_4$-alkyl or $C_1$-$C_4$-haloalkyl;

$R^{10}$ is $C_1$-$C_4$-alkylsulfonyl;

$R^{11}$ is hydrogen;

$R^{12}$ is $C_1$-$C_4$-alkyl;

$R^{13}$ is hydrogen.

8. A composition as claimed in claim 1, comprising at least one safener C selected from the group consisting of benoxacor, cloquintocet, dichlormid, fenchlorazole, fenclorim, fluxofenim, furilazole, isoxadifen, mefenpyr, 2,2,5-trimethyl-3-(dichloroacetyl)-1,3-oxazolidine and oxabetrinil, or an agriculturally acceptable salt thereof, or an ester, amide or thioester of such safeners C which have a carboxyl group.

9. A composition as claimed in claim 1, wherein the weight ratio of component A to component B is in the range from 10:1 to 1:500.

10. A composition as claimed in claim 1, wherein the weight ratio of component A to component C is in the range from 10:1 to 1:10.

11. A composition as claimed in claim 1, wherein the weight ratio of component B to component C is in the range from 50:1 to 1:10.

12. A composition as claimed in claim 1 in the form of a crop protection composition comprising additionally at least one inert liquid and/or solid carrier, if desired at least one surfactant and, if appropriate, customary auxiliaries.

13. A composition as claimed in claim 1 in the form of a crop protection composition formulated as a 2-component composition comprising a first component which comprises the active compound A, a solid or liquid carrier and, if appropriate, one or more surfactants, and a second component which comprises at least one further active compound selected from the herbicides B and the safeners C, a solid or liquid carrier and, if appropriate, one or more surfactants.

14. A method for controlling undesirable vegetation, which comprises allowing a herbicidally effective amount of a composition as claimed in claim 1 to act on plants, their habitat or on seed.

15. A method as claimed in claim 14, wherein the composition is applied before, during and/or after emergence of the undesirable plants, the herbicidally active components A), B) and C) being applied simultaneously or successively.

16. A method as claimed in claim 15, wherein the leaves of the crop plants and the undesirable plants are treated.

17. The method of claim 14 in crops of cereals.

18. The method of claim 14 in crops of corn and in crops of sorghum.

19. The method of claim 14 in crops of rice.

20. The method of claim 14 in crops of cotton, in crops of oilseed rape, in crops of soyabean, in crops of potatoes, in crops of dry beans, in crops of groundnuts and in perennial crops.

21. The method of claim 14 in forestry.

22. The method of claim 14 in crops of plants where the crop plants are resistant to one or more herbicides owing to genetical engineering and/or breeding.

23. The method of claim 14 in crops of plants where the crop plants are resistant to attack by insects owing to genetical engineering and/or breeding.

24. A method for the desiccation and/or defoliation of plants, which comprises allowing an effective amount of a composition as claimed in claim 1 to act on the plants, their habitat or on seed.

25. A composition as claimed in claim 1, wherein the at least one herbicide B is selected from:
   b1) lipid biosynthesis inhibitors;
   b2) acetolactate synthase inhibitors (ALS inhibitors);
   b3) photosynthesis inhibitors;
   b4) protoporphyrinogen-IX oxidase inhibitors;
   b5) bleacher herbicides;
   b6) glyphosate;
   b7) glufosinate and bilanaphos;
   b9) benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;
   b10) inhibitors of the synthesis of very long chain fatty acids (VLCFA inhibitors);
   b11) dichlobenil, chlorthiamid, isoxaben and flupoxam;
   b13) auxin herbicides;
   b14) naptalam and diflufenzopyr;
   b15) benzoylprop, flamprop, flamprop-M, bromobutide, chlorflurenol, cinmethylin, methyldymron, etobenzanid, fosamine, metam, pyributicarb, oxaziclomefone, dazomet, triaziflam and methyl bromide.

26. A composition as claimed in claim 1, wherein the at least one herbicide B is selected from:
   b1) lipid biosynthesis inhibitors;
   b2) acetolactate synthase inhibitors (ALS inhibitors);
   b3) photosynthesis inhibitors;
   b4) protoporphyrinogen-IX oxidase inhibitors;
   b5) bleacher herbicides;
   b6) glyphosate;
   b7) glufosinate and bilanaphos;
   b9) benfluralin, butralin, dinitramine, ethalfluralin, oryzalin, pendimethalin, trifluralin and propyzamide;
   b10) inhibitors of the synthesis of very long chain fatty acids (VLCFA inhibitors);
   b11) dichlobenil, chlorthiamid, isoxaben and flupoxam;
   b13) auxin herbicides;
   b14) diflufenzopyr;
   b15) bromobutide, cinmethylin, methyldymron, oxaziclomefone and triaziflam.

* * * * *

UNITED STATES PATENT AND TRADEMARK OFFICE
CERTIFICATE OF CORRECTION

PATENT NO.         : 7,375,058 B2
APPLICATION NO. : 10/488977
DATED                 : May 20, 2008
INVENTOR(S)       : Zagar et al.

It is certified that error appears in the above-identified patent and that said Letters Patent is hereby corrected as shown below:

On the title page item (75), line 3:
    "Ouakenbush" should read --Quakenbush--
In Claim 5, col. 51, indicated line 15:
    "fenoxa-prop" should read --fenoxaprop--
In Claim 5, col. 51, indicated line 65:
    "chiomethoxyfen" should read --chlomethoxyfen--
In Claim 5, col. 52, indicated line 2:
    "cinidonethyl" should read --cinidon-ethyl--
In Claim 5, col. 52, indicated lines 8-9:
    "metfiurazon" should read --metflurazon--
In Claim 5, col. 52, indicated line 51:
    "ethalfiuralin" should read --ethalfluralin--
In Claim 5, col. 52, indicated line 62:
    "xylachbor" should read --xylachlor--
In Claim 5, col. 52, indicated line 67:
    "dichiobenil" should read --dichlobenil--
In Claim 5, col. 53, indicated line 5:
    "quincborac" should read --quinclorac-- and
    "cbopyralid" should read --clopyralid--
In Claim 5, col. 53, indicated line 6:
    "tricbopyr" should read --triclopyr--
In Claim 6, col. 53, indicated line 41:
    "propanhl" should read --propanil--
In Claim 6, col. 53, indicated line 48:
    "pyraclonhl" should read --pyraclonil--
In Claim 6, col. 53, indicated line 66:
    "ethalfiuralin" should read --ethalfluralin--

UNITED STATES PATENT AND TRADEMARK OFFICE
CERTIFICATE OF CORRECTION

PATENT NO. : 7,375,058 B2
APPLICATION NO. : 10/488977
DATED : May 20, 2008
INVENTOR(S) : Zagar et al.

It is certified that error appears in the above-identified patent and that said Letters Patent is hereby corrected as shown below:

In Claim 6, col. 54, indicated line 4:
"thenyichlor" should read --thenylchlor--

Signed and Sealed this

Fifth Day of August, 2008

JON W. DUDAS
*Director of the United States Patent and Trademark Office*